(12) United States Patent
Fitzpatrick

(10) Patent No.: US 9,078,673 B2
(45) Date of Patent: Jul. 14, 2015

(54) METHOD OF HUMERAL HEAD RESURFACING AND/OR REPLACEMENT AND SYSTEM FOR ACCOMPLISHING THE METHOD

(71) Applicant: Michael J. Fitzpatrick, Laguna Beach, CA (US)

(72) Inventor: Michael J. Fitzpatrick, Laguna Beach, CA (US)

(73) Assignee: Ortho Innovations, Inc., Laguna Beach, CA (US)

( * ) Notice: Subject to any disclaimer, the term of this patent is extended or adjusted under 35 U.S.C. 154(b) by 162 days.

(21) Appl. No.: 13/745,519

(22) Filed: Jan. 18, 2013

(65) Prior Publication Data

US 2013/0197523 A1    Aug. 1, 2013

Related U.S. Application Data

(60) Provisional application No. 61/588,152, filed on Jan. 18, 2012.

(51) Int. Cl.
*A61B 17/17* (2006.01)
*A61B 17/16* (2006.01)
*A61F 2/40* (2006.01)

(52) U.S. Cl.
CPC .............. *A61B 17/1721* (2013.01); *A61B 17/16* (2013.01); *A61B 17/1684* (2013.01); *A61B 17/1739* (2013.01); *A61B 17/175* (2013.01);
(Continued)

(58) Field of Classification Search
CPC ........... A61B 17/1664; A61B 17/1666; A61B 17/1668; A61B 17/1721; A61B 17/17; A61B 17/1742; A61B 17/1746; A61B 17/175; A61B 17/1753; A61B 2017/1778; A61B 17/1662; A61B 17/1684; A61F 2/4612
USPC ................... 606/80, 81, 86 R, 87, 89, 96, 99; 623/19.11–19.14

See application file for complete search history.

(56) References Cited

U.S. PATENT DOCUMENTS 2,682,265 A * 6/1954 Collison ..................... 623/23.11
3,704,707 A * 12/1972 Halloran ......................... 606/97
4,037,592 A * 7/1977 Kronner .......................... 606/97

(Continued)

OTHER PUBLICATIONS

Ruedi, T., von Hochstetter, A.H.C., and Schlumph, R., "Surgical Approaches for Internal Fixation", 1984, Springer-Verlag, pp. VII and 12.*

(Continued)

*Primary Examiner* — Kevin T Truong
*Assistant Examiner* — Amy Sipp
(74) *Attorney, Agent, or Firm* — K. David Crockett, Esq.; Crockett & Crockett, PC

(57) ABSTRACT

A method, and devices for facilitating the method, for shoulder replacement surgery. The method entails establishing a mechanical support in a the anatomical neck plane of the proximal humeral head, fixing a jig to the mechanical support, where the jig supports a drill guide with its axis perpendicular to the anatomical neck plane, adjusting the drill guide it coincide with the axis of the humeral head, drilling a hole through the humeral head for insertion of a shaft which will support and rotate a reaming bit. The reaming bits used to resurface the humeral head and the glenoid fossa are inserted through the back of the patient, through a gap created between two easily separated muscles, rather than through a gap cut through the subscapularis muscle on the front of the joint. A suitable jig is provided to facilitate the method.

14 Claims, 21 Drawing Sheets

(52) U.S. Cl.
CPC ....... *A61B 2017/1778* (2013.01); *A61F 2/4014* (2013.01); *A61F 2/4081* (2013.01)

(56) References Cited

U.S. PATENT DOCUMENTS

| | | | | |
|---|---|---|---|---|
| 4,722,331 | A * | 2/1988 | Fox | 606/96 |
| 5,725,593 | A * | 3/1998 | Caracciolo | 623/22.23 |
| 5,800,557 | A * | 9/1998 | Elhami | 623/23.12 |
| 6,231,611 | B1 * | 5/2001 | Mosseri | 623/22.12 |
| 6,395,005 | B1 * | 5/2002 | Lovell | 606/91 |
| 6,511,481 | B2 * | 1/2003 | von Hoffmann et al. | 606/67 |
| 6,679,916 | B1 * | 1/2004 | Frankle et al. | 623/19.12 |
| 7,070,601 | B2 * | 7/2006 | Culbert et al. | 606/71 |
| 7,621,962 | B2 * | 11/2009 | Lakin | 623/22.15 |
| 7,909,882 | B2 * | 3/2011 | Stinnette | 623/23.41 |
| 8,419,744 | B2 * | 4/2013 | Petit et al. | 606/99 |
| 8,636,745 | B2 * | 1/2014 | Almutairi et al. | 606/96 |
| 2002/0095214 | A1 * | 7/2002 | Hyde, Jr. | 623/18.12 |
| 2003/0212405 | A1 * | 11/2003 | Choi | 606/98 |
| 2005/0043805 | A1 * | 2/2005 | Chudik | 623/19.14 |
| 2005/0107799 | A1 * | 5/2005 | Graf et al. | 606/91 |
| 2005/0154398 | A1 * | 7/2005 | Miniaci et al. | 606/96 |
| 2007/0005074 | A1 | 1/2007 | Chudik | |
| 2007/0038302 | A1 * | 2/2007 | Shultz et al. | 623/19.11 |
| 2008/0021479 | A1 * | 1/2008 | Penenberg | 606/96 |
| 2008/0306601 | A1 * | 12/2008 | Dreyfuss | 623/19.14 |
| 2009/0105838 | A1 * | 4/2009 | Russo et al. | 623/19.14 |
| 2010/0191247 | A1 * | 7/2010 | Schneider | 606/96 |
| 2010/0298834 | A1 * | 11/2010 | Hildebrandt | 606/80 |
| 2011/0152868 | A1 * | 6/2011 | Kourtis et al. | 606/80 |
| 2012/0089233 | A1 * | 4/2012 | Capon et al. | 623/19.13 |
| 2012/0109322 | A1 * | 5/2012 | Gonzalez-Hernandez | 623/19.14 |

OTHER PUBLICATIONS

Brodsky, et al., Simplified Posterior Approach to the Should Joint, 69-A J. Bone and Joint Surgery 773 (1987).

\* cited by examiner

ANTERIOR

ANTERIOR

METHOD OF HUMERAL HEAD RESURFACING AND/OR REPLACEMENT AND SYSTEM FOR ACCOMPLISHING THE METHOD

This application claims priority to U.S. Provisional Application 61/588,152 filed Jan. 18, 2012.

FIELD OF THE INVENTIONS

The inventions described below relate the field of shoulder surgery.

BACKGROUND OF THE INVENTIONS

Shoulder replacement surgery and shoulder resurfacing surgery are used to treat severe arthritis or physical damage to the shoulder joint. In shoulder replacement surgeries, the head of the humerus is replaced with a metal ball. The glenoid fossa may also replaced with a plastic socket, covered with a new plastic surface, or ground smooth. When both components are replaced, this is referred to as a total shoulder replacement. When the head is replaced without treatment of the glenoid, this is referred to as a hemiarthroplasty. In shoulder resurfacing, the head of the humerus is ground smooth and covered with a metal cap (a resurfacing hemiarthroplasty), or just ground down. The glenoid fossa may also be ground smooth and covered with a plastic surface.

To accomplish shoulder replacement or resurfacing, a surgeon must gain surgical access to the joint. This is currently achieved from the front of the patient, in a deltopectoral approach, by cutting through the skin (a delta pectoral incision), separating the deltoid and pectoralis major muscles and pushing the cephalic vein aside, cutting through the subscapularis muscle on the front of the joint, cutting through conjoint tendon and the biceps tendon, cutting through circumflex blood vessels (arteries and veins), and cutting through the subscapularis tendon (or subscapularis muscle) and other tissues surrounding the joint to open to the joint capsule surrounding the humeral head. The joint capsule is then cut open to expose the humeral head and glenoid fossa.

With the humeral head exposed, the surgeon dislocates the shoulder to twist the humerus so that the humeral head points forward and is exposed, and pops it out of the shoulder to expose it to the reamers and saws needed to prepare the humeral head.

With the humeral head exposed, the surgeon will punch a hole in the intramedullary canal of the humerus to support a saw guide, and cut the round head of the humerus off using the saw guide to ensure a clean, flat cut across the anatomical neck. With the semispherical portion of the head removed, the surgeon inserts a long metal stem into the bone (into the intramedullary canal), and screws the metal half-ball onto the stem. This structure replaces the humeral head.

To replace the glenoid socket, the surgeon uses a reamer with a convex outer surface, to grind the glenoid socket to the shape desired to accommodate the glenoid socket prosthesis. The surgeon then drills several holes in the remaining glenoid socket to accommodate the several posts on the underside of the prosthesis. The surgeon inserts a drill guide into the exposed joint space, and then drill several holes in the glenoid socket. With the holes prepared, the surgeon inserts the glenoid socket prosthesis into the prepared glenoid socket. Access to the glenoid socket requires significant dislocation of the shoulder joint, to move the humerus out of the way.

In a resurfacing surgery, the head of the humerus is not cut off, but is instead ground smooth with a hemispherical reamer and covered with a metal cap. To accomplish this, the surgeon inserts a rigid guidewire into the center of the head of the exposed humerus, and drives the pin into the head, then through the humeral head. The surgeon then positions the hemispherical reamer over the humeral head and rotates it with a drill to grind the humeral head surface. The drill shaft extends outwardly from the apex of the humeral head, so that the reamer and drill can only be applied after dislocation of the shoulder to point the apex out of the joint. The inner surface of the reamer is the same shape as the cap, so that when the reaming is complete the remaining bone of the humeral head is the same shape as the inside of the cap. When reaming is complete, the surgeon secures the cap over the humeral head. The glenoid fossa may be replaced, resurfaced, or debrided to complete the procedure. Shoulder resurfacing is more conservative than should replacement because it requires removal of less bone from the humerus.

The procedure is usually successful in relieving pain and restoring some range of motion vis-à-vis the limited range of motion in the diseased shoulder. However, because muscles and tendons of the shoulder joint are cut, patients often suffer from severely restricted range of motion vis-à-vis the natural range of motion. Although any surgical exposure runs the low risk of injury to the neurovascular structures during surgical dissection and exposure, the anterior deltopectoral approach has a high incidence of subscapularis dysfunction (i.e. weakness) because of the transection of the tendon during the planned surgical exposure. By some reports, there is a 75% incidence of significant weakness of the subscapularis muscle even after a well-performed shoulder replacement.

SUMMARY OF THE INVENTIONS

The methods and devices described below provide for access to the shoulder joint for shoulder replacement or resurfacing surgery while eliminating the need for cutting of muscle or tendon, thereby limiting the risk of nerve damage inherent in the currently used anterior approach to the surgery. The method entails gaining access to the shoulder joint through a dissected gap between the infraspinatus and teres minor muscles in the back of the shoulder, without cutting through these muscles. The method is facilitated by installation of a jig, which entails establishing a mechanical support in the anatomical neck plane of the proximal humeral head by inserting a pair of pins in the humeral head, within the anatomical neck plane, mounting a frame on the pins which in turn supports a drill guide with its axis perpendicular to the anatomical neck plane. The drill guide is adjusted so that it coincides with the axis of the humeral head. The surgeon then drills a bore hole through the humeral head along this axis. This bore hole is used for the insertion of a shaft which will support and rotate a surfacing bit or reaming bit. The reaming bits used to resurface the humeral head and the glenoid fossa are inserted through the back of the patient, through a gap created between the infraspinatus and teres minor muscles, rather than through a gap cut through the subscapularis muscle on the front of the joint. The reaming bits are driven by a drill shaft disposed within the humeral head, inserted from the lateral aspect of the humerus, with the drill attached to the drill shaft located laterally relative to the humerus, rather than a drill shaft approaching the humeral head from the medial aspect.

A suitable jig is provided to facilitate the method. A jig, as used in mechanical arts, is any device for accurately guiding and positioning a drill or other tool in relation to the workpiece, or for positioning the parts of an object during assembly. In this case, the workpiece is the humeral head. The jig includes the pins, frames and drill guides used to properly position the drill bit needed to establish the bore hole in the humeral head. This bore hole extends from the lateral aspect of the humeral head, and extends superiorly and medially (upwards and inwards) to the apex of the humeral head (that point which corresponds to the apex of the planned humeral head prosthesis). To aid in initial placement of the pins in the anatomical neck plane, the surgery is preceded by arthroscopic exploration, in which the anatomical neck, apex of humeral head, anterior articular border, are marked.

DETAILED DESCRIPTION OF THE INVENTIONS

Figure 1:
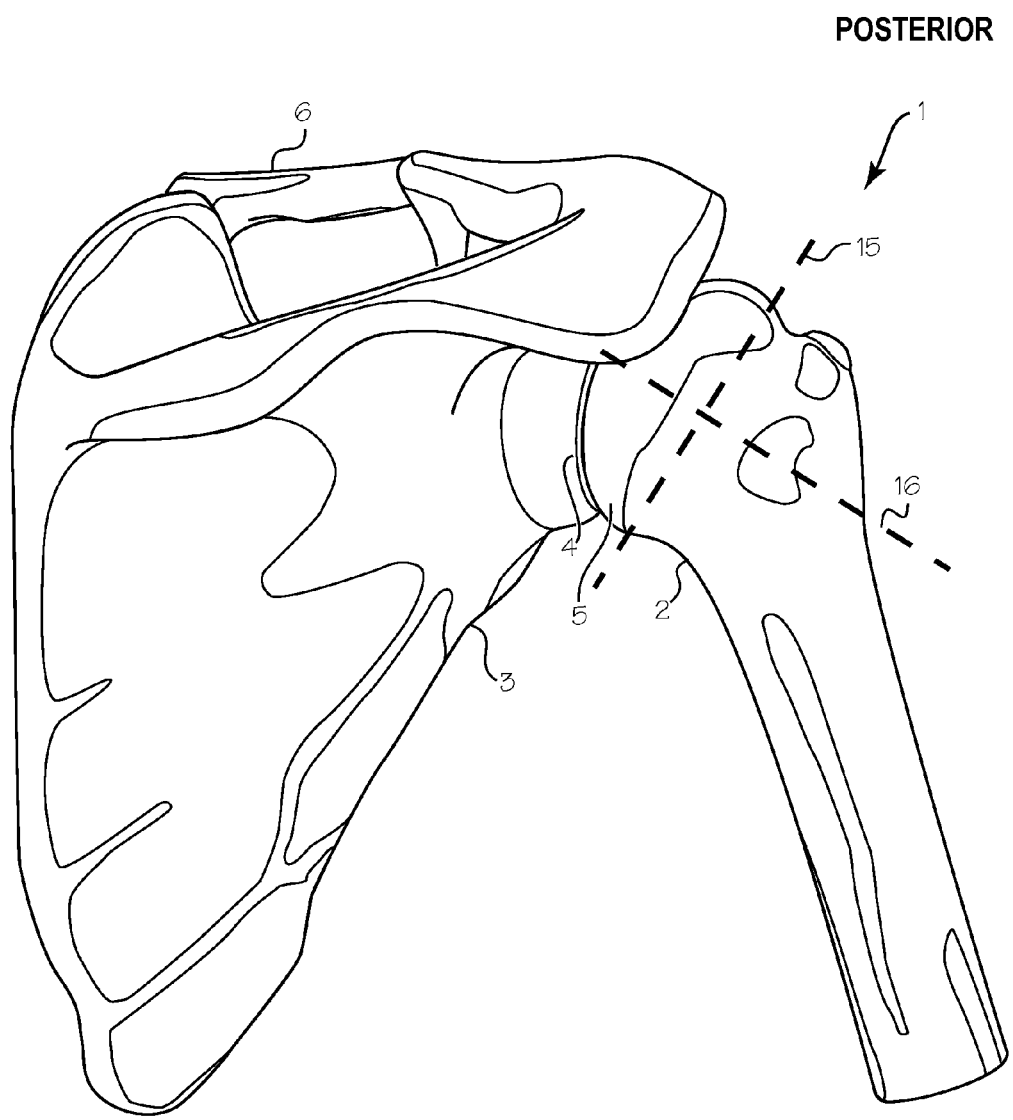
FIG. 1 is a posterior view of the shoulder joint.
Figure 2:
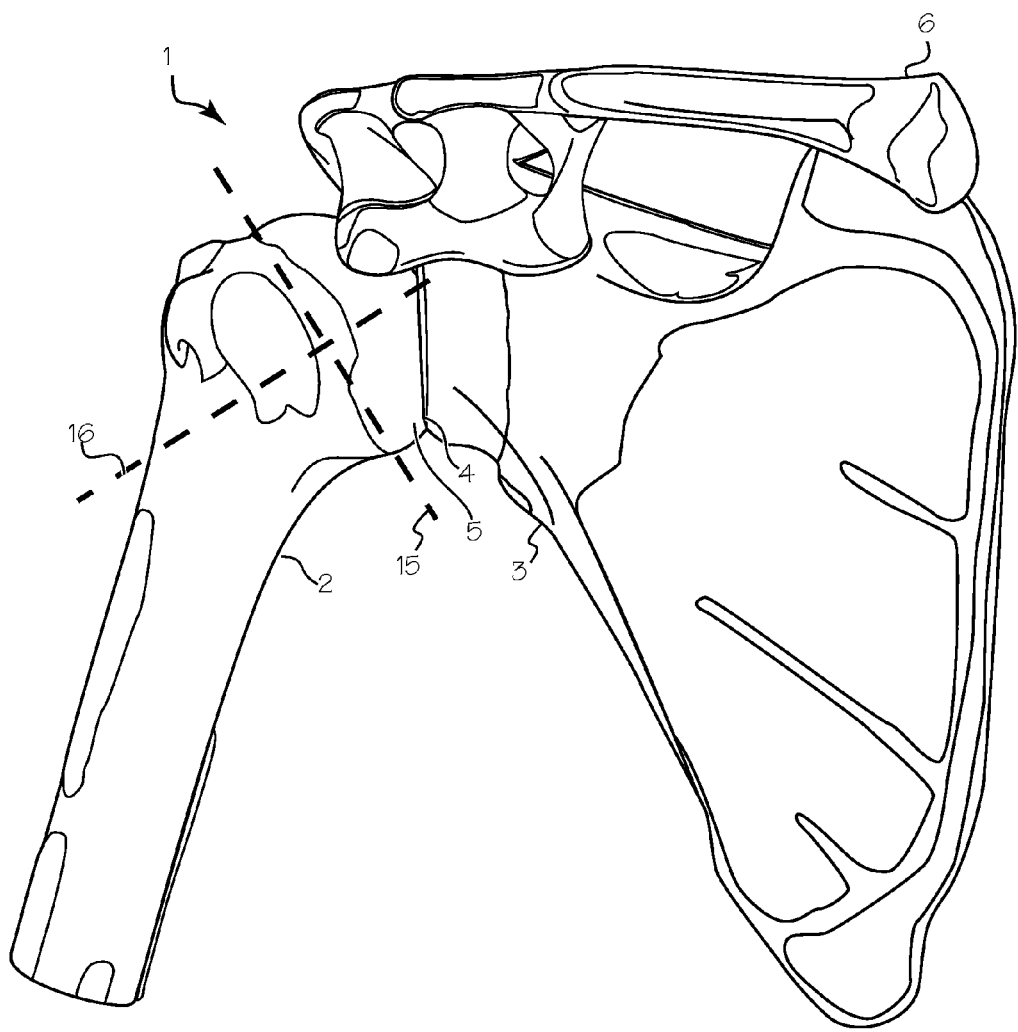
FIG. 2 is an anterior view of the shoulder joint.

FIG. 1 is a posterior (back) view of the shoulder 1. The major landmarks include the humerus 2 and the scapula 3, the glenoid fossa 4 and the head 5 of the humerus, the clavicle 6 and the acromonion 7. The humeral head is a roughly semispherical mass that fits within a corresponding socket of the glenoid fossa. Together, the humeral head and the glenoid fossa comprise the gleno-humeral joint. FIG. 2 is a corresponding anterior (front) view of the shoulder, showing the same landmarks. The goal of the devices and methods described in this application is to facilitate the remodeling and/or replacement of the surfaces of the humeral head and glenoid fossa. To gain access to the gleno-humeral joint, various layers of tissue (skin, muscle, tendons and ligaments) must be penetrated.

Figure 3:
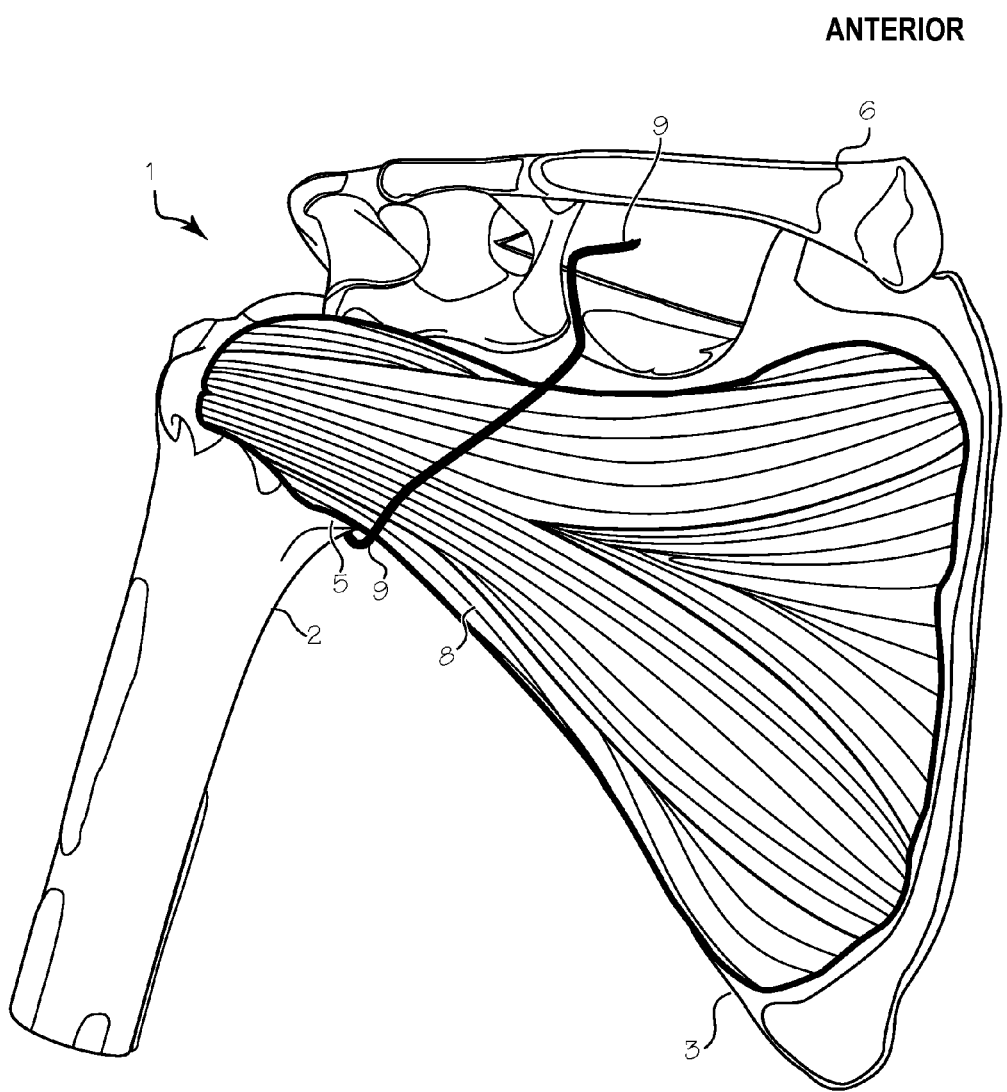
FIG. 3 is an anterior view of the shoulder joint showing the muscles that cover the joint.

As shown in FIG. 3, the anterior surface of the gleno-humeral joint is covered by the lateral portion of the subscapularis muscle 8. The axillary nerve, illustrated by the black line 9, runs from the neck, under the subscapularis muscle, under the shoulder joint and posteriorly into the back muscles illustrated in FIG. 4.

Figure 4:
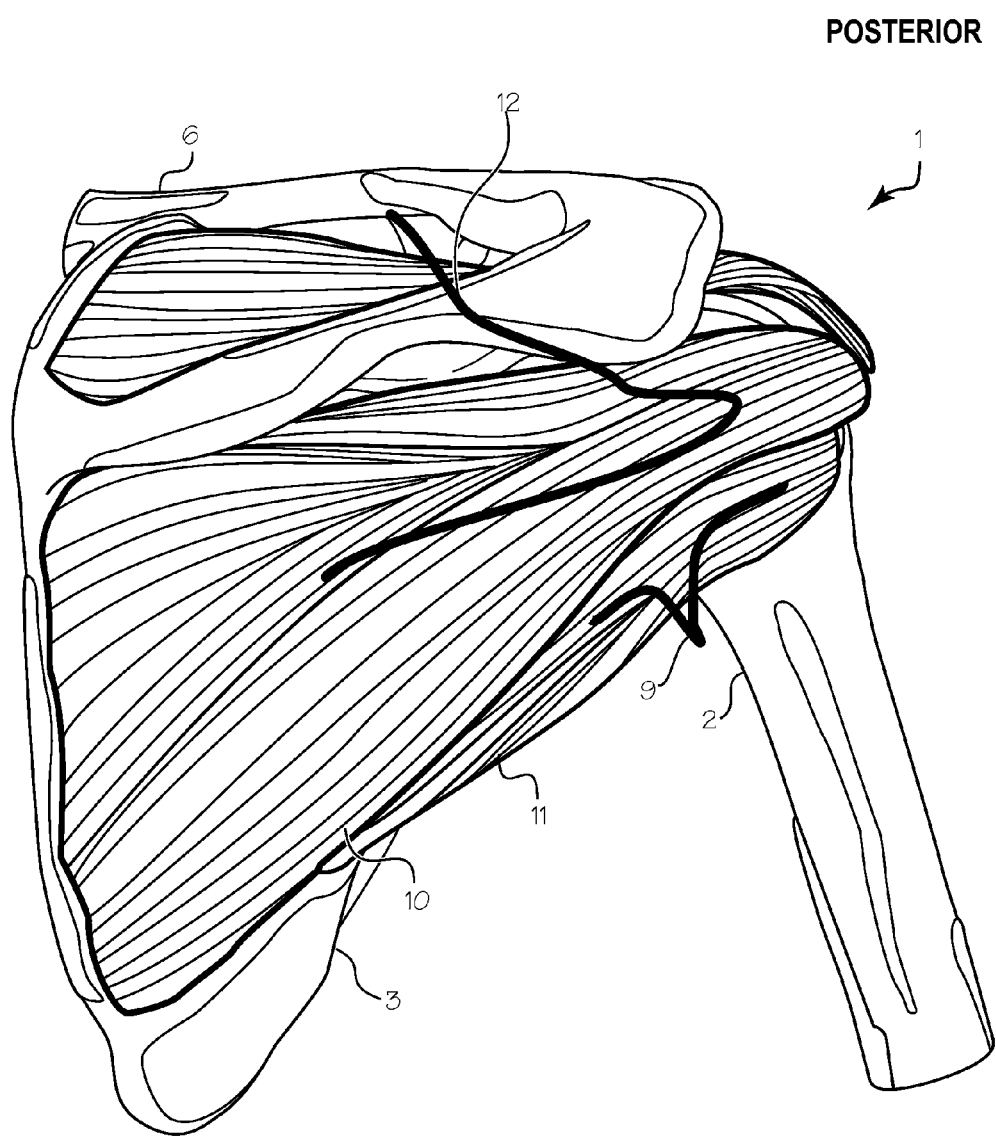
FIG. 4 is an posterior view of the shoulder joint showing the muscles that cover the joint.

As shown in FIG. 4, the posterior surface of the gleno-humeral joint is covered by the infraspinatus muscle 10. The teres minor muscle 11 underlies the infraspinatus muscle and also covers a portion of the gleno-humeral joint. In this posterior view of FIG. 4, a portion of the supraspinatus muscle is visible, arching over the superior surface of the gleno-humeral joint. The suprascapular nerve 12 is illustrated by the black line, and runs over the top of the scapula, downwardly and laterally within the infraspinatus muscle, and turns medially within the infraspinatus muscle. The suprascapular nerve innervates both the supraspinatus muscles and infraspinatus muscles. The axillary nerve 9, continuing from the front of the shoulder, runs upwardly into the teres minor and branches medially and laterally. The lateral branch also enervates the deltoid muscle. The surgical procedures described in this application provide for access to the gleno-humeral joint while avoiding damage to these nerves.

As a precursor to the main joint replacement/resurfacing surgery, the surgeon will examine and pretreat the humeral/glenoid joint with an arthroscopic procedure, in which the surgeon inserts an arthroscope into the joint capsule to view the humeral head and glenoid fossa. Under arthroscopic guidance, the surgeon places one or two pins in the plane of the humeral head (the anatomical neck plane). The position for at least one pin is marked, and a pilot hole or starter hole (a small dent will serve as a starter hole, which provides a small indentation in the bone to trap the point of the pin to prevent walking during insertion). The surgeon also identifies and marks anatomical landmarks involved in the procedure, including the desired apex of the humeral head and the anterior articular border. The apex is the center point of the hemispherical shape of the head, and establishes or corresponds to the desired axis of the prosthetic metal ball that will replace the head. The surgeon may also remove any bone spurs in the joint and repair other defects while the joint is inflated.

Figure 5:
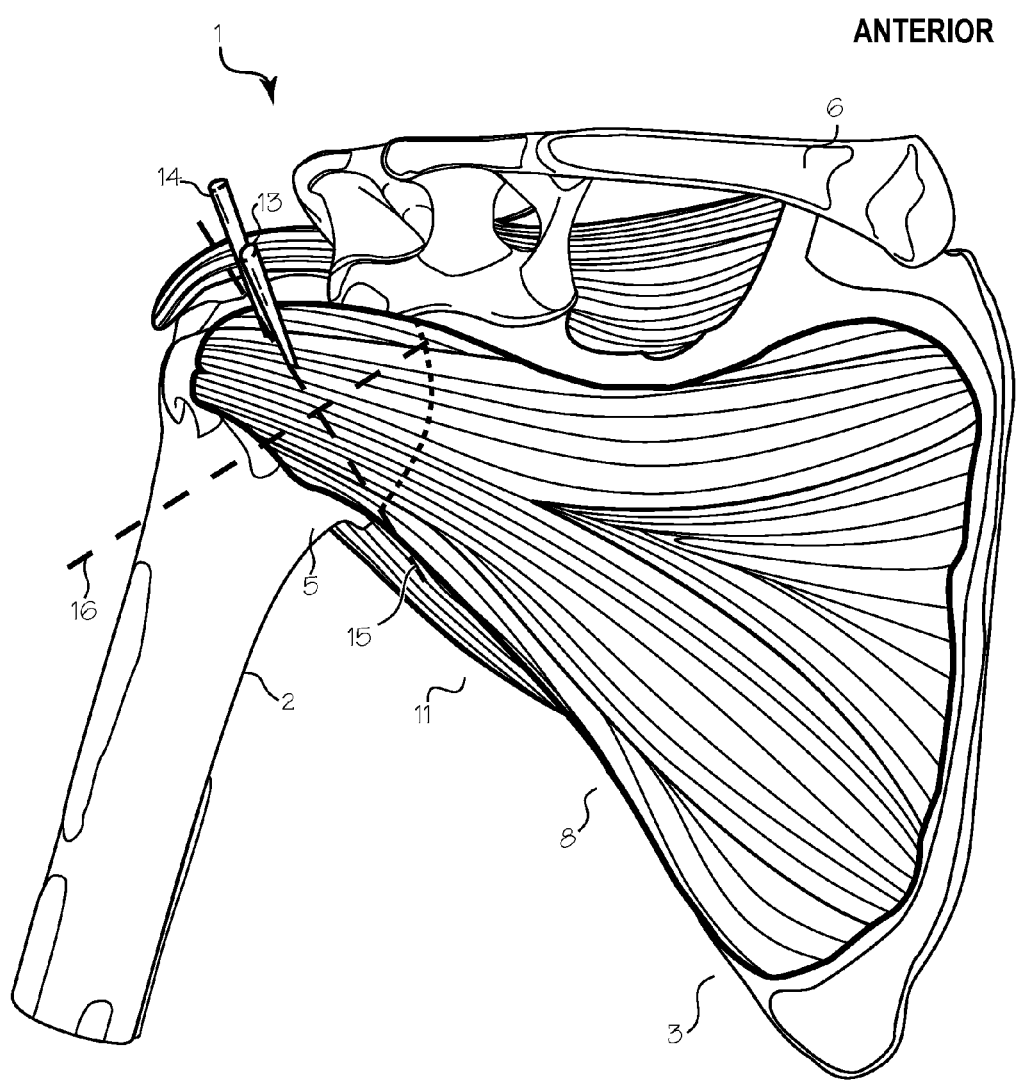
FIG. 5 is an anterior view of the shoulder joint illustrating the insertion of pins to establish a working plane corresponding to the anatomical neck plane at the base of the head of the humerus.

FIG. 5 is an anterior view of the shoulder joint illustrating the insertion of pins to establish a working plane corresponding to the anatomical neck plane (the base of the head of the humerus). FIG. 5 illustrates a first step in the procedure which provides access to the gleno-humeral joint. This step is preferably accomplished in an arthroscopic procedure, using an arthroscope to view the placement of the pins and inflating the joint space with distension fluid to facilitate viewing and access. Placement under arthroscopic visualization assures precise placement of the starting points for the pins. In this step, two Schanz pins 13 and 14 are inserted into the humeral head. The pins are inserted along the anatomical neck plane, which is a plane at the base of the humeral head (at or near the articular cartilage/anatomic neck border) that is perpendicular to the intended axis of the resurfaced humeral head, or the original axis of the existing humeral head (the bottom of the replacement prosthesis will lie in this plane or a parallel plane, and the axis of replacement prosthesis or resurfacing prosthesis will be perpendicular to this plane). This plane is shown by the phantom plane 15 shown in FIGS. 5 and 6 and other Figures. (This plane is based on the individual anatomy, and is selected by the surgeon as the best approximation of a plane separating the articular surface of the humeral head and the footprints of attachment of various muscles to the base of the humeral head.) A single pin may be used, especially if it is provided with a large flat head or other means of unambiguously aligning a portion of the pin with the anatomical neck plane. This placement will be accomplished by the surgeon, and the determination of the appropriate plane will be made by the surgeon, taking into account the existing shape of the humeral head and glenoid fossa, and the shapes of replacement parts. As used in this application, the term "axis" of the humeral head refers generally to a line through the humeral head, from its apex, through the humeral head, such that the roughly spherical humeral head is centered on that line, or the intended prosthesis will be centered on that line. Its exact location is determined by the surgeon. The axis is preferably substantially perpendicular to the anatomical neck plane, and the anatomical neck plane may be chosen with the desired axis in mind. The pin and dotted line 16 shown in FIG. 1 and other figures illustrate this axis.

Figure 6:
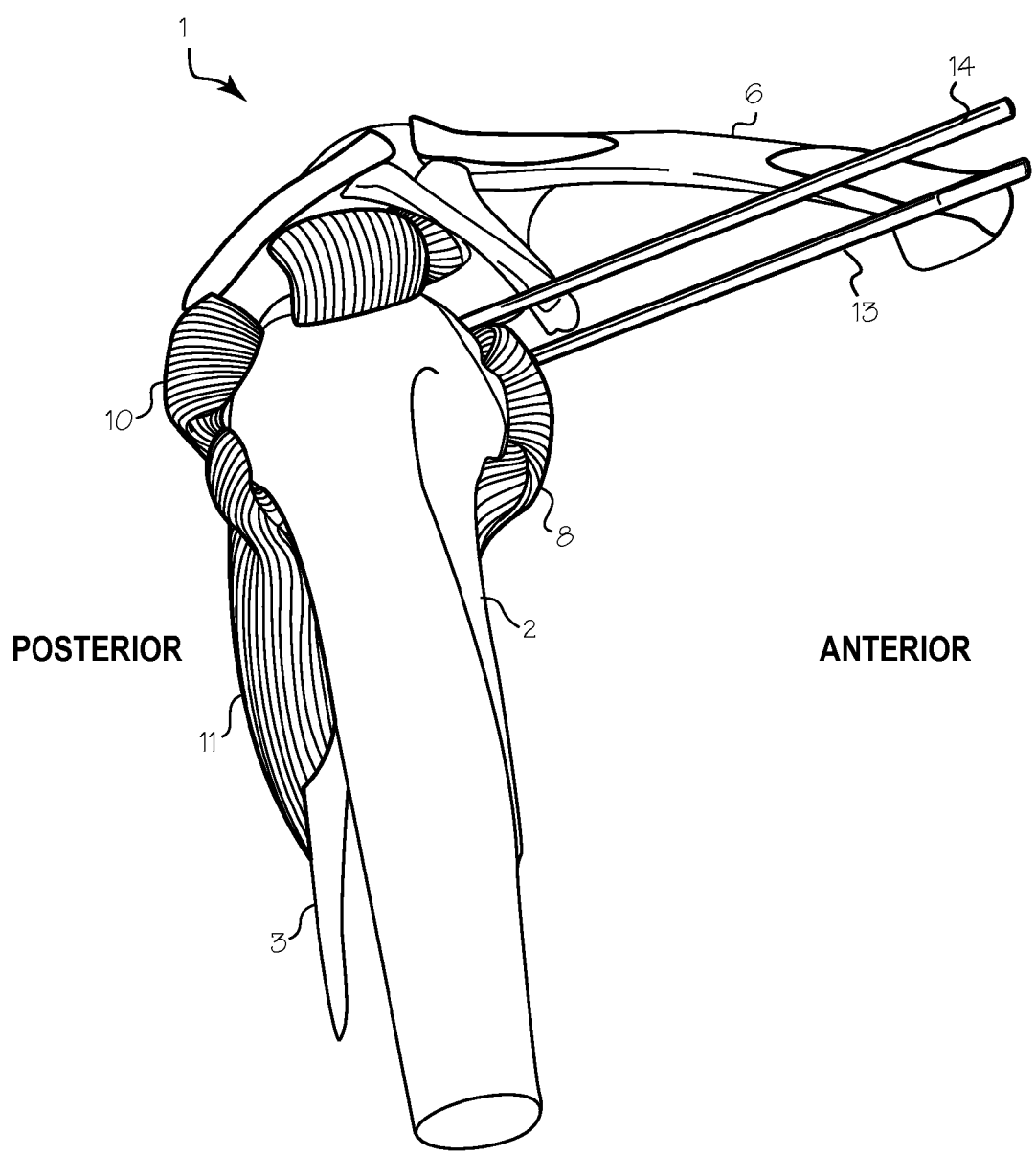
FIG. 6 is a lateral view of the shoulder joint illustrating the insertion of pins to establish a working plane corresponding to the base of the head of the humerus.

FIG. 6 is a lateral view, corresponding to the view of FIG. 5, of the shoulder joint illustrating the insertion of pins 13 and 14 to establish a working plane corresponding to the base of the head of the humerus.

Figure 7:
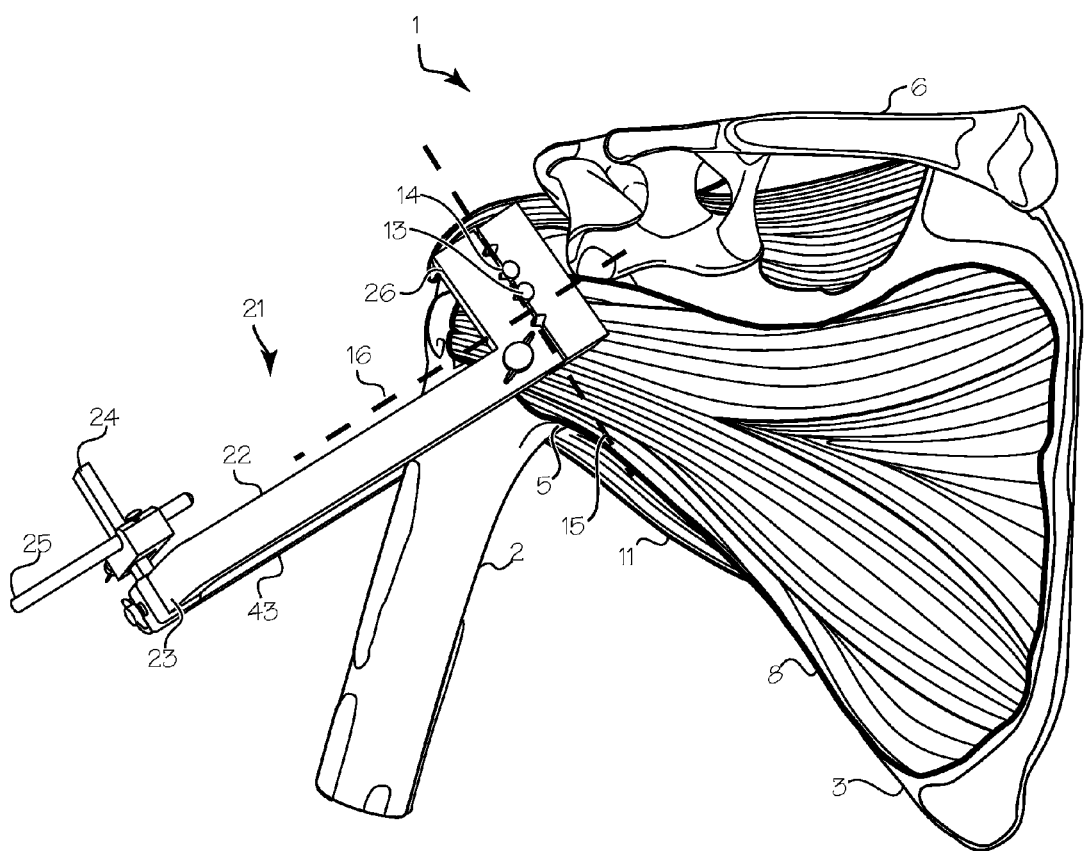
FIG. 7 is an anterior view of the shoulder joint illustrating the placement of a jig on the pins establishing the working plane corresponding to the base of the head of the humerus, to locate a drill guide in a plane perpendicular to the base of the head and centered on the central axis of the humeral head.

FIG. 7 is an anterior view of the shoulder joint illustrating the placement of a jig 21 on the pins 13 and 14 establishing the working plane corresponding to the base of the head of the humerus, to establish a plane perpendicular to the base of the head and centered on the central axis of the humeral head. The jig, which in this case comprises three perpendicularly arranged straight segments 22, 23 and 24, holds a drill guide 25 on the axis of the humeral head (as determined by the surgeon). The frame is fixed to the Schanz pins with the clamp 26. The clamp includes parallel grooves or channels, sized to accept the pins 13 and 14, either directly or through pin guides (shown in FIG. 12). Through this arrangement, the drill guide is perpendicular to the Schanz pins 13 and 14 and the plane established by those two pins. The frame illustrated in FIG. 7 is a unitary frame, in meaning that all the segments are formed integrally, or fused together so that may be handled as a single component. The frame lies in a plane perpendicular to the anatomical neck plane, and this plane may be coincident to the humeral head axis or just above or below the plane (as necessary to accommodate the structural attachment of the drill guide to the frame). The drill guide 25 is slidably mounted on the third segment 24, so that it is fixed in the plane of the frame, with its axis perpendicular to the anatomical neck plane and parallel to the humeral head axis. The drill guide may be adjusted, up and down relative to the plane, so that it is coaxial with the humeral head axis (that is, it lies on the same line as the humeral head axis such that a drill bit passing through the guide will drill a hole along the humeral head axis).

Figure 8:
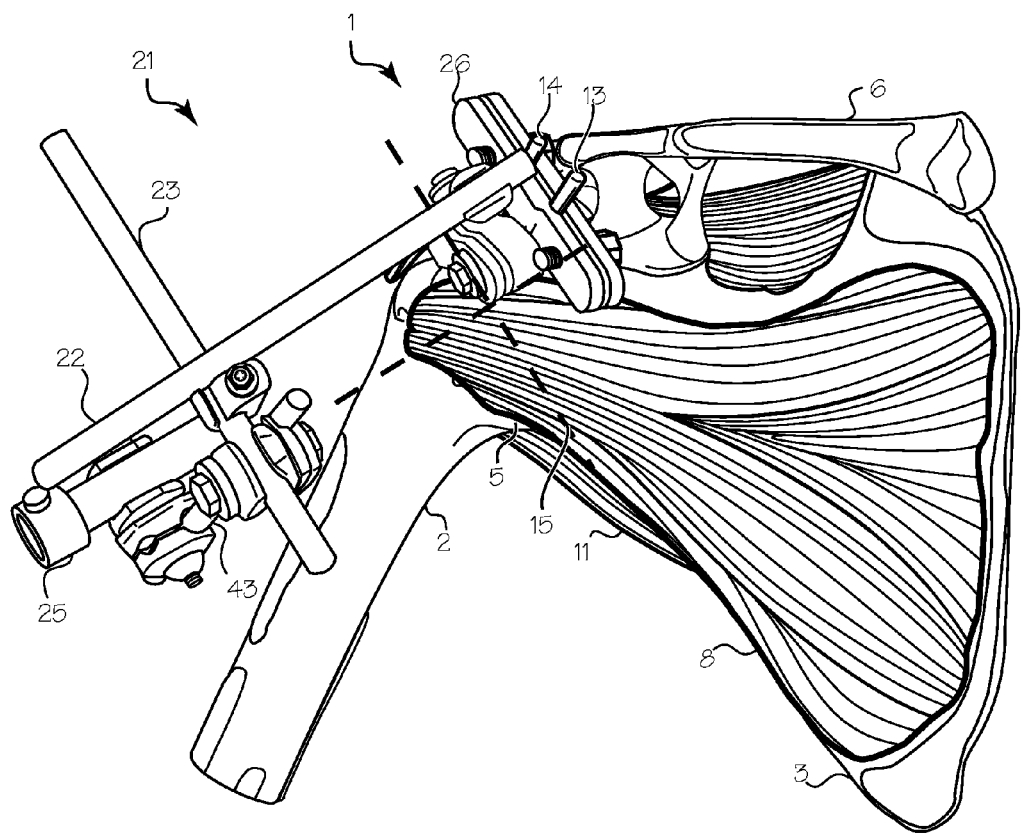
FIG. 8 illustrates a rudimentary embodiment of the frame of FIG. 7.

FIG. 8 illustrates a rudimentary embodiment of the frame. The jig, which in this embodiment comprises three perpendicularly arranged segments comprising straight rods 27, 28 and 29, holds a drill guide 25 on the axis of the humeral head. The rods are fixed to the Schanz pins with the clamp 26. The rods are perpendicular to each other, and fixed with clamps 30. Thus, the first rod 27 is secured perpendicular to the Schanz pins with the clamp 30, and the second rod 28 is secured perpendicularly to the first rod with the clamp 31, and the third rod 29 is secured perpendicularly to the second rod with the clamp 32. Finally, the drill guide 25 is secured perpendicularly to the third rod through clamp 33. Through this arrangement, the drill guide is perpendicular to the Schanz pins 13 and 14 and the plane established by those two pins. Slight adjustments of the third rod 29 of the frame (which is parallel to the Schanz pins and perpendicular to the second rod) along the second rod 28, which is preferably perpendicular to the Schanz pin 13 and 14, but in a plane parallel to the plane established by those two pins, can be used to align the drill guide with the axis of the humeral head. The third rod is also translatable along the second rod, so that the drill guide may be aligned with the axis of the humeral head by moving the third rod in a generally anterior to posterior direction along the second rod. The drill guide is translatable along the third pin, and rotatable about the third rod, so that is may be aligned with the axis of the humeral head. Likewise, translation of the second rod, in a substantially lateral to medial direction, and translation of the first rod, along the Schanz pins, can be used to align the drill guide with the axis of the humeral head.

The purpose of the pin placement is to establish a known geometric relationship between the anatomical neck plane and the jig, and hence the drill guide. The placement of the pins is depicted in the anatomical neck plane. However, the pins may be placed elsewhere, so long as the jig is modified to receive the pins and still hold the drill guide in proper position. This is most conveniently done by placing the pins along the anatomical neck plane which can be identified using anatomical landmarks. Also, the assembly of perpendicular rods is just one mechanism that may be used co-locate the drill guide with the axis of the humeral head. The frames of FIGS. 7 and 8 are merely examples of frames devised to place the drill guide on the axis of the humeral head, using the pins as a basis for establishing the anatomical neck plane. The frame may be a unitary square frame as shown in FIG. 7, a multi-component frame as shown in FIG. 8, or any suitable rigid structure, including a single arcuate assembly, that ensures proper coaxially placement of the drill guide with the humeral head axis.

Figure 9:
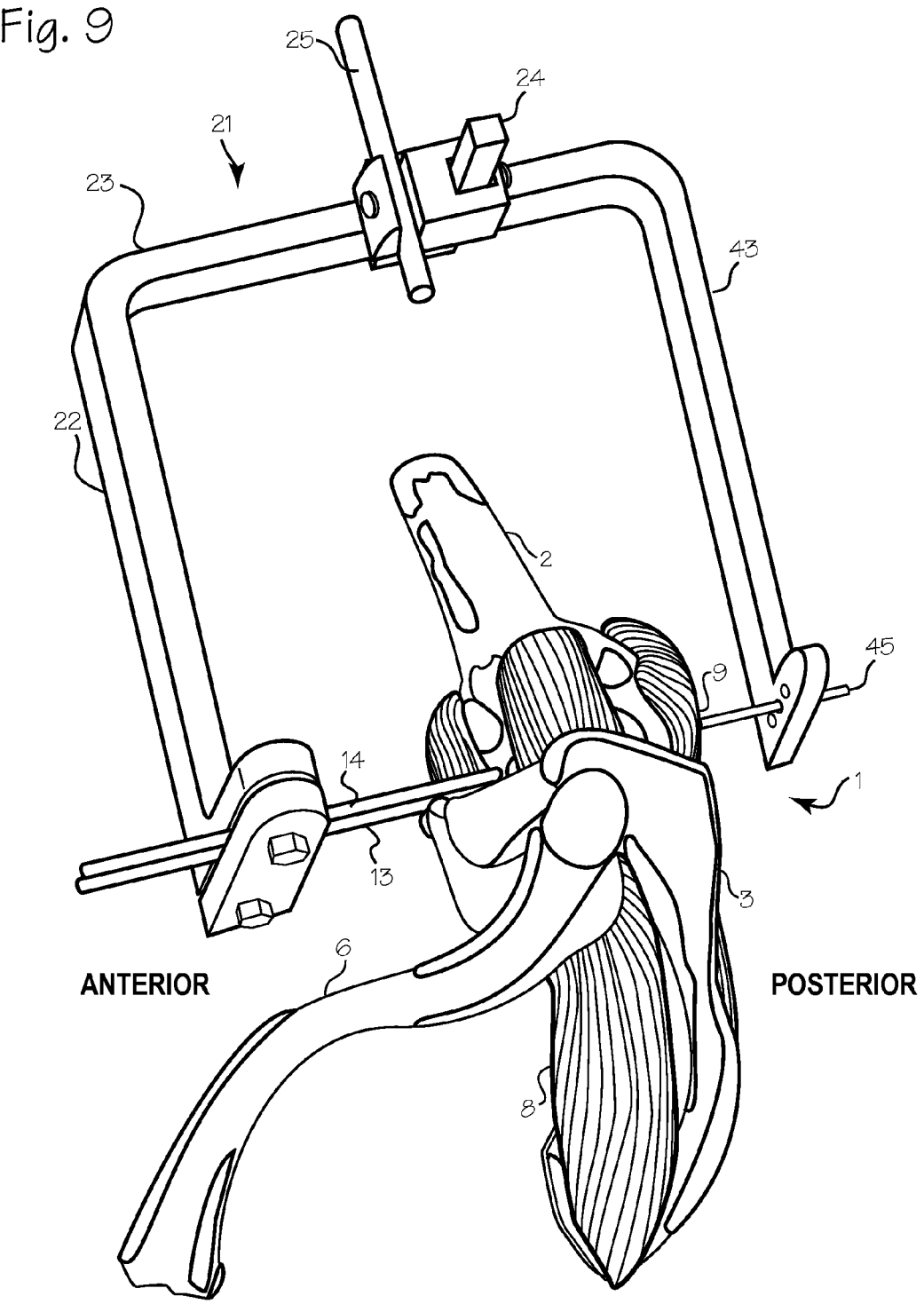
FIG. 9 is a superior view, corresponding to FIG. 7, of the shoulder joint illustrating the placement of a jig on the pins establishing the working plane corresponding to the base of the head of the humerus.

FIG. 9 is a superior view, corresponding to FIG. 7, of the shoulder joint illustrating the placement of a jig on the pins establishing the working plane corresponding to the base of the head of the humerus, to establish a plane perpendicular to the base of the humeral head and centered on the central axis of the humeral head. In this superior view, the second segment 23 is more clearly visible.

Figure 10:
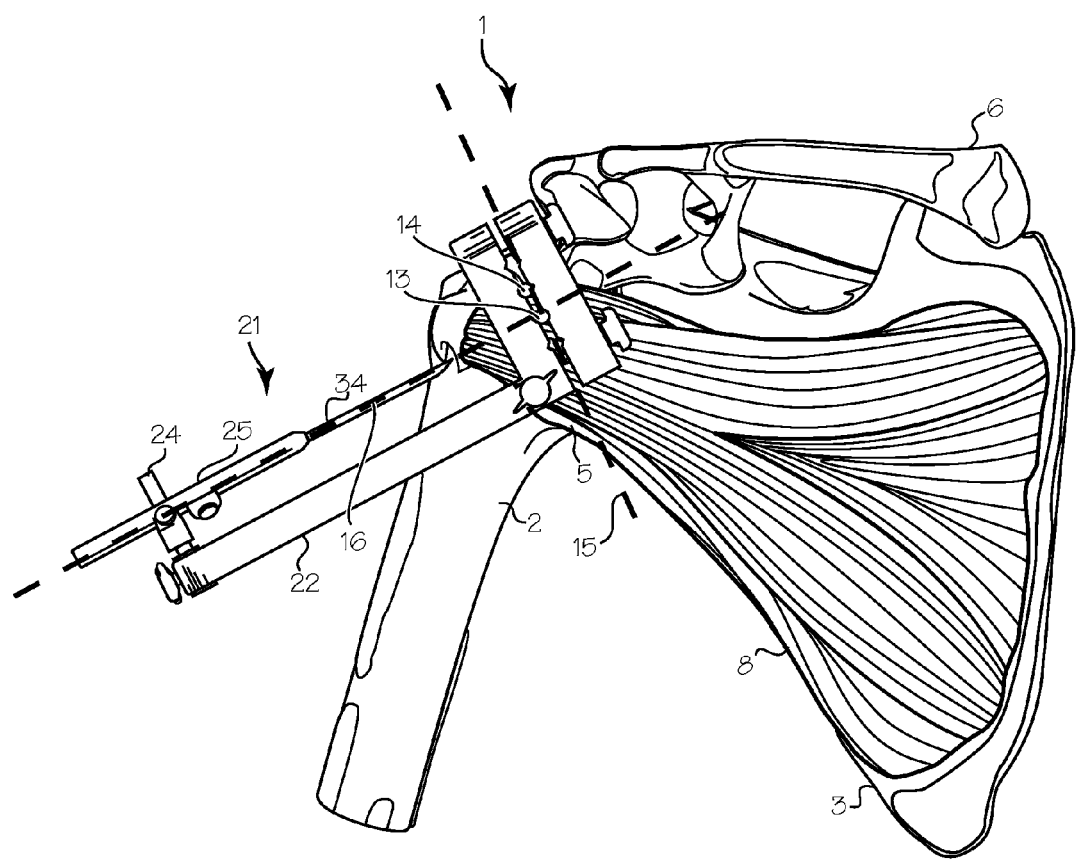
FIG. 10 is an anterior view of the shoulder joint illustrating insertion of a drill in the jig establishing the plane perpendicular to the anatomical neck plane (the base of the humeral head) and centered on the axis of the humeral head.
Figure 16:
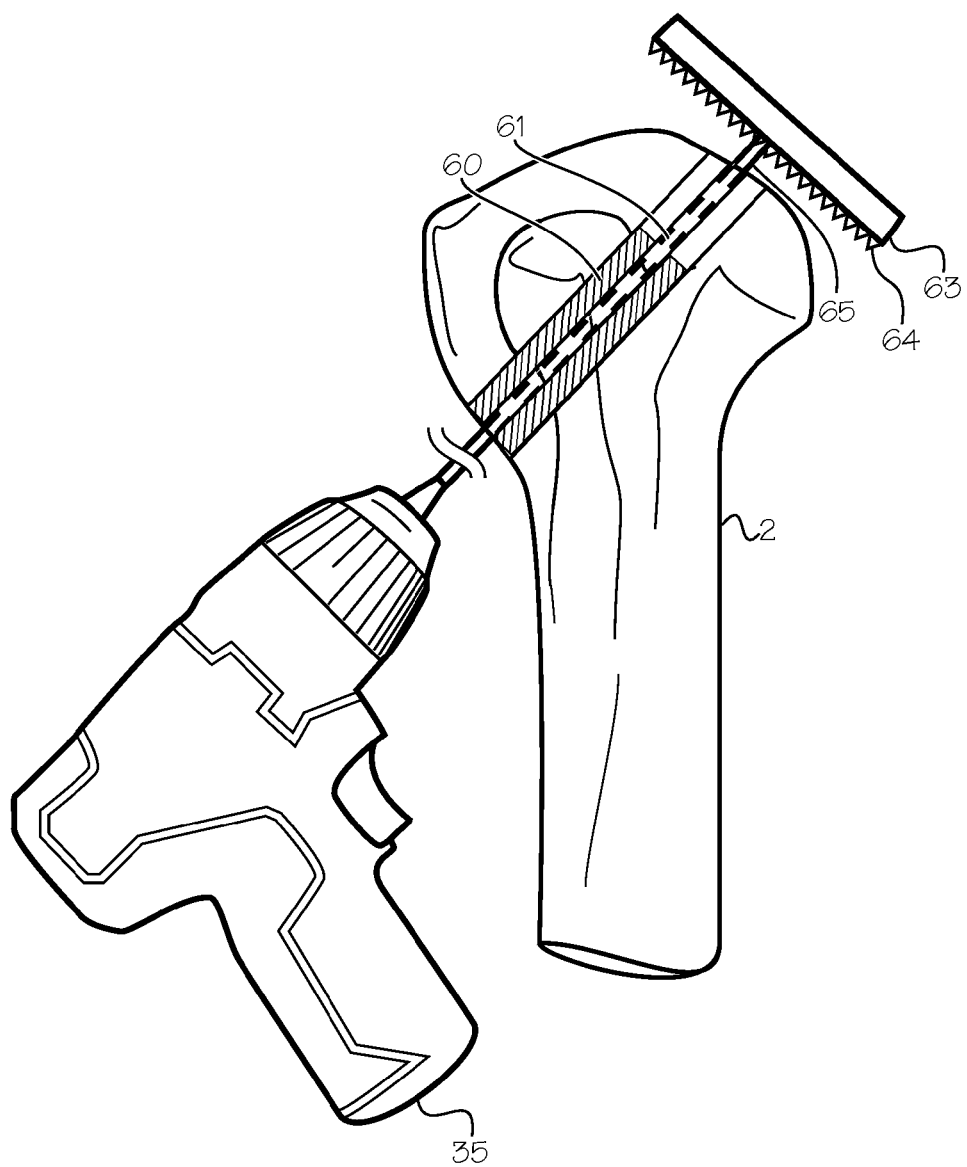
FIGS. 16 and 17 illustrate the use of a new flat humeral head reamer bit to remove the humeral head.

FIG. 10 is an anterior view of the shoulder joint illustrating insertion of a drill bit 34 in the drill guide 25 of the jig establishing the plane perpendicular to the base of the head and centered on the central axis of the humeral head. The drill guide 25 has been located and aligned with the axis of the humeral head, and is generally perpendicular to the working plane established by the Schanz pins. A drill bit is inserted through the drill guide, and is driven by the drill (item 35 in FIG. 16) to create a bore hole through the humerus and humeral head along the axis of the humeral head.

Figure 11:
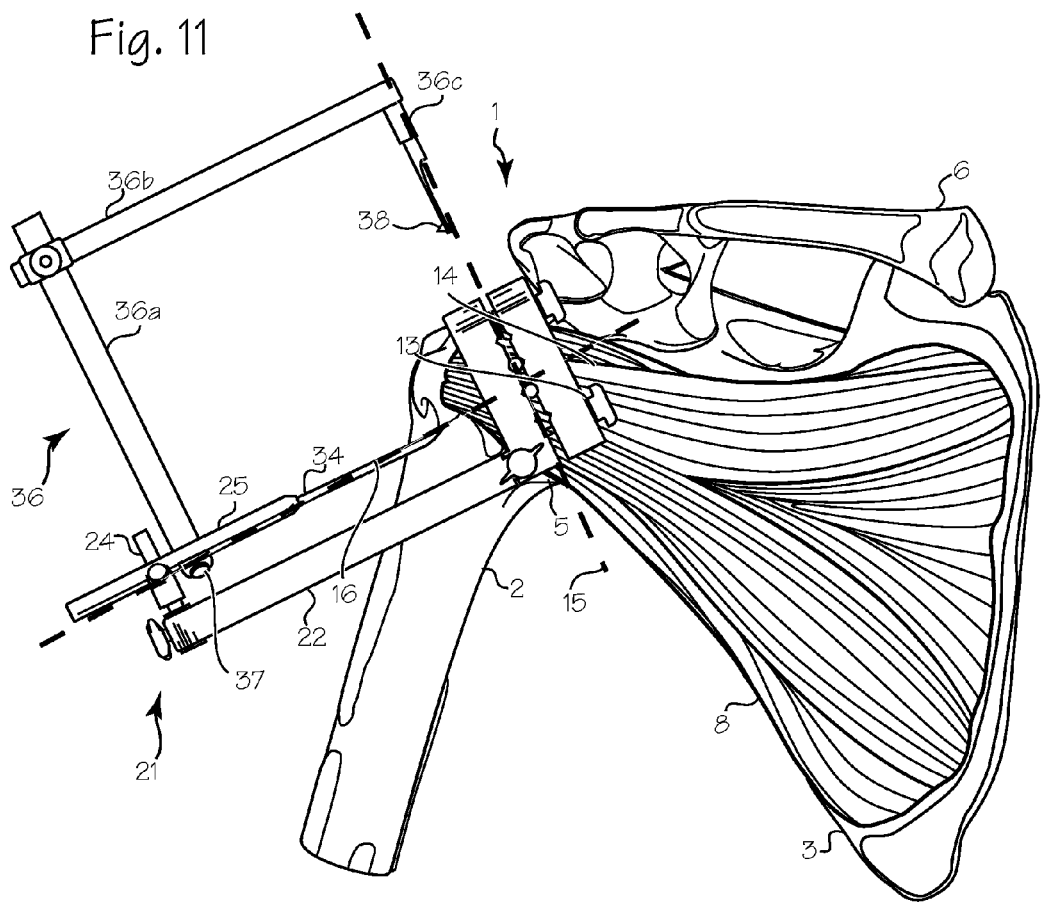
FIG. 11 is an anterior view of the shoulder joint illustrating an additional jig that may optionally be used to ensure that the drill guide is coaxially located with the axis of the humeral head.

FIG. 11 is an anterior view of the shoulder joint illustrating an additional jig 36 that may optionally be used to ensure that the drill guide is coaxially located with the humeral head axis. The jig is secured to the drill guide 25 (or any convenient portion of the jig) with set screw 37 in a receiving channel of frame segment 36a (the receiving channel and set screw act as a clamp). This jig includes a locator pin 38 fixed on frame segment 36c which is sized and dimensions such that, when the jig is attached securely to the drill guide, the point of the locator pin is aligned with the central axis of the drill guide. Frame segment 36b can be translated along frame segment 36a, through the clamp 36d as needed to bring the locator pin into contact with the humeral head. (Frame segment 36c is configured, along with the remaining frame segments, to locate the locator pin on the axis of the drill guide, but is shortened in the Figure for illustration.) The second jig 36 can be rotated relative to the first jig 21 (about the drill guide), as needed to position the frame segment 36c to enter the joint, while still maintaining frame segment 36c parallel to the anatomical neck plane and maintaining the pin locator 38 coaxial with the drill guide 25. Preferably, the surgeon will insert the frame segment 36c through the posterior aspect of the shoulder, through the infraspinatus-teres minor interval created as described in relation to FIG. 15. The second jig can be rotated anteriorly or superiorly if the surgeon desires to have the frame segment 36c enter the joint anteriorly or superiorly. If the apex of the humeral head has been marked during the initial arthroscopic inspection, placement of the pin on this mark will ensure that the drill guide is properly aligned. If the head of the apex has not been marked previously, the surgeon can mark it after the joint is opened, or use the locator pin to mark it. Again, as with the jig 21, this additional jig may be made of several component parts fixed together with clamps, or made of a single arcuate frame which may be fixed to the jig 21 directly, rather than the drill guide.

Figure 12:
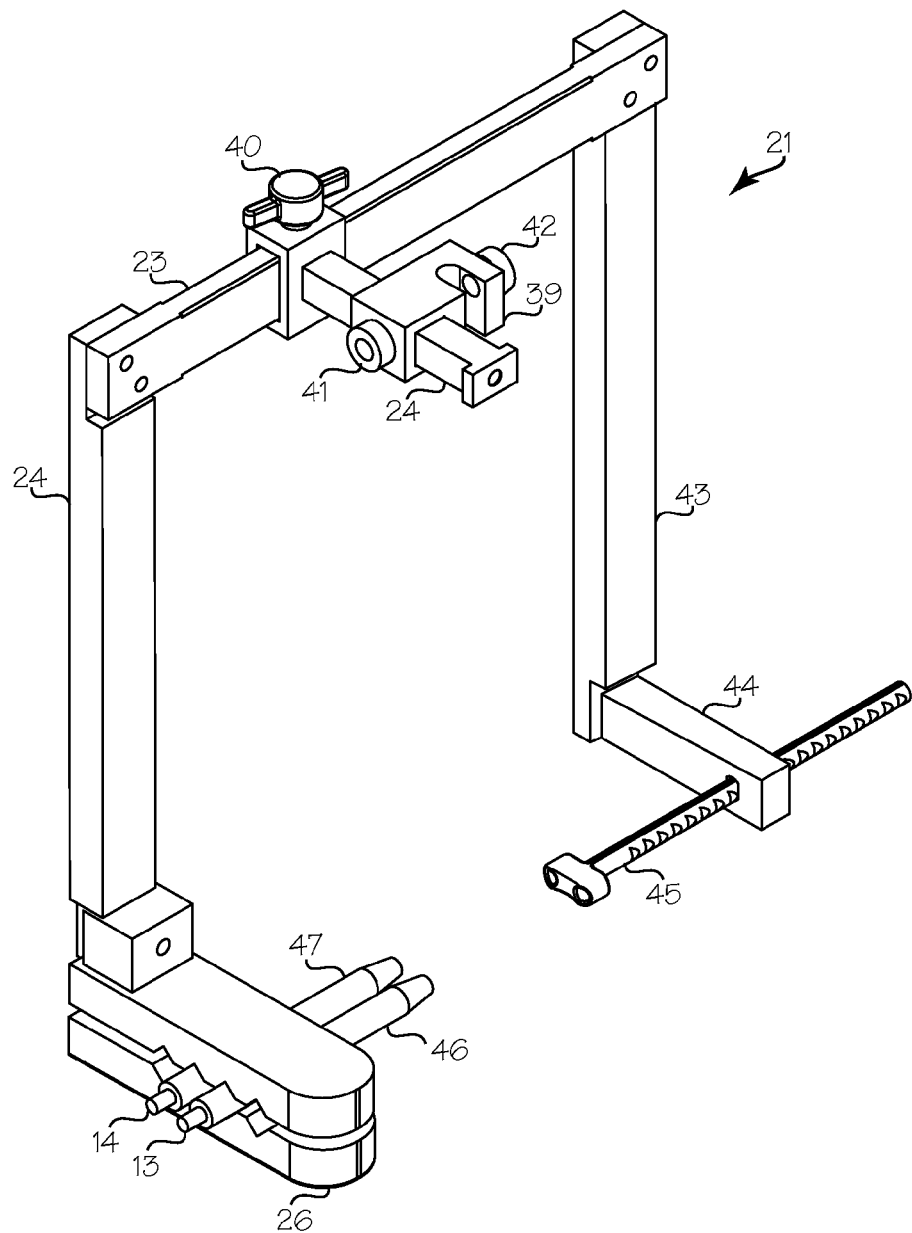
FIGS. 12, 13 and 14 illustrate the jigs used in the previous Figures, with additional features that facilitate the surgery.
Figure 13:
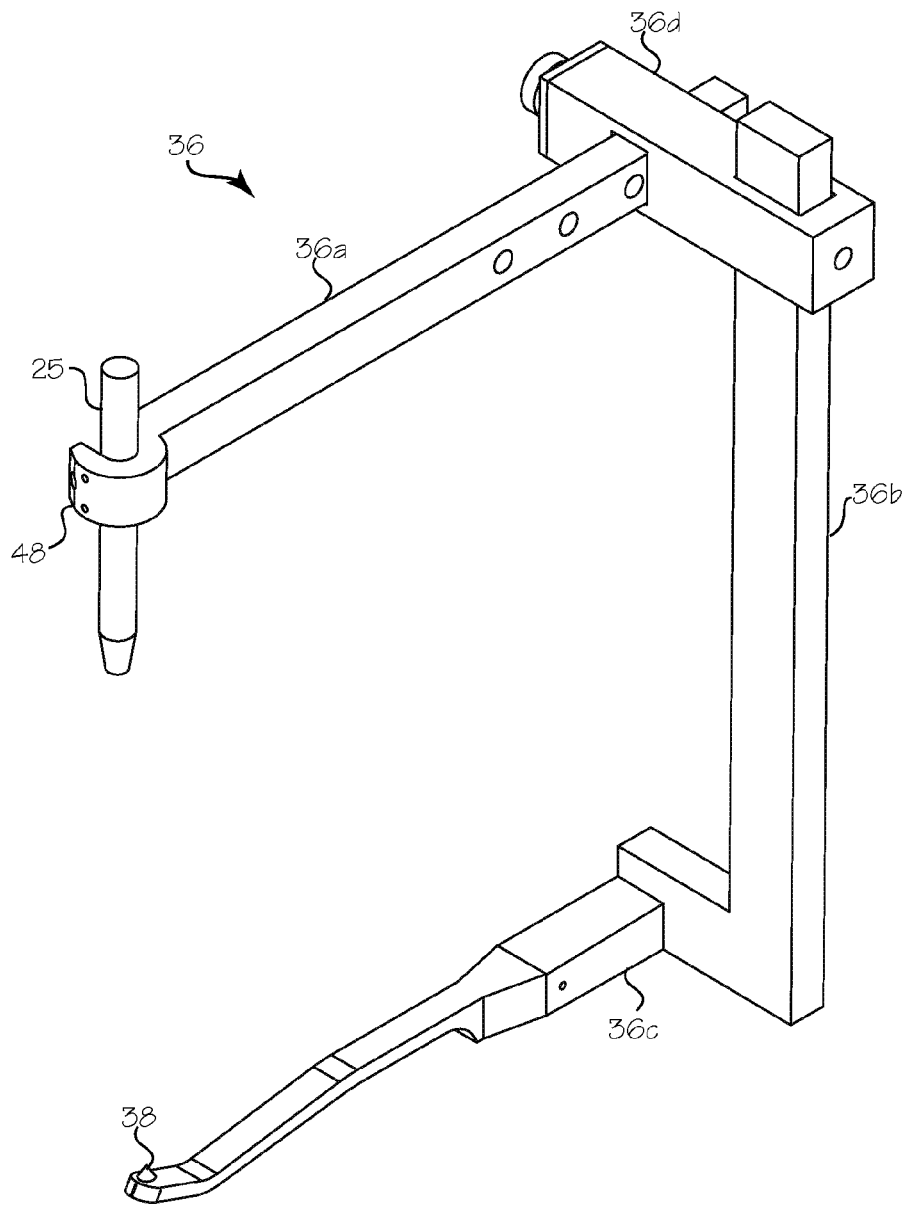
Figure 14:
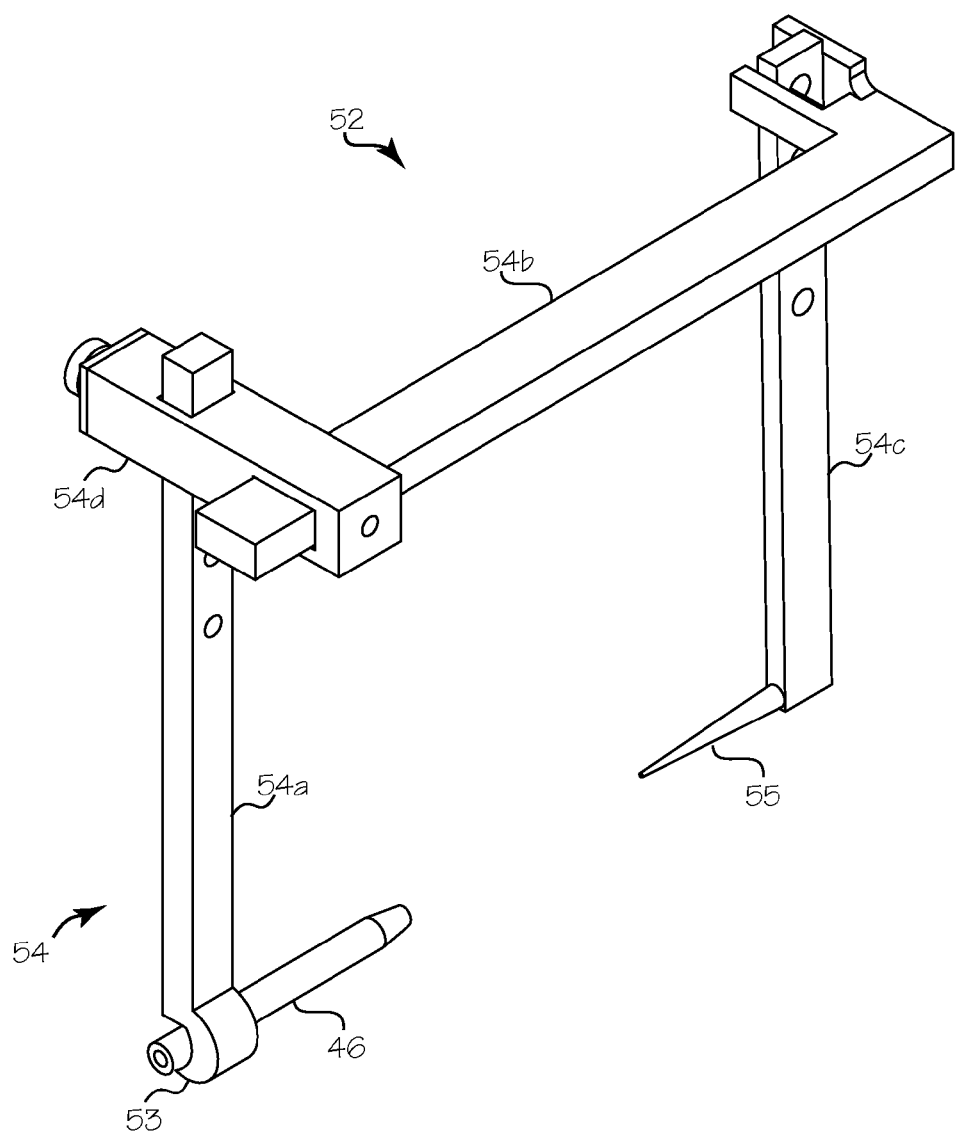

The jigs are illustrated in isolation in FIGS. 12 through 14. FIG. 12 shows a version of the jig 21 used to locate the drill guide in proper perpendicular relationship to the anatomical neck plane. This jig includes the clamp 26 configured to securely fix the jig to the pins 13 and 14, and an arch comprising perpendicular segments 22, 23 and 24 which position the drill guide receiver 39 with its bore perpendicular to the anatomical neck plane. The third segment 24 is slidably mounted on the second segment 23, which lies parallel to the neck plane, so that it can be moved along the second segment until it (or the plane it occupies) intersects the humeral axis, and is secured with set screw 40. The drill guide receiver is slidably mounted on the third segment 24, which also lies parallel to the neck plane, so that it can be moved along the third segment until it is aligned with the humeral axis, and is secured in place with set screw 41. The drill guide 25 is disposed within the receiver, and secured with the set screw 42. This version of the jig includes a fourth and fifth perpendicularly arranged segments 43 and 44 (the fourth segment is perpendicular to the third segment, and the fifth segment is perpendicular to the fourth segment) and pin receiver 45. This receiver is slidably disposed on frame segment 44, along the plane established by the Schanz pins, which coincides with the anatomical neck plane. The receiver includes one or more bores, positioned to be coaxial to the Schanz pins, which can receive the Schanz pins.

Additional pin guides 46 and 47 may be provided. One pin guide can be placed over the first Schanz pin that is installed by the surgeon, perhaps using the jig illustrated in relation to FIG. 14. This pin guide can be used as a cannula to ease placement of the Schanz pin, or can be placed over the Schanz pin. After the first pin is placed, and secured also in the bore of the pin receiver 45, and the pin guide 46 is in place over first pin 13, the surgeon can clamp the first jig 21 to the first pin guide, with the second pin guide 47 in place (or placed afterward) in the clamp and held in the anatomical neck plane, the surgeon may insert the second pin 14 through the humeral head, running through the second pin guide 47, through the humeral head (on the anatomical neck plane) and into the corresponding bore on the receiver 45. This securely establishes the pins in the anatomical neck plane. With both pins secured within the clamp, the humeral head and the receiver, the frame which holds the drill guide 25 is firmly held in the desired position, perpendicular to the anatomical neck plane, and may be translated along frame segments 28 and 29 as needed to position the drill guide along the humeral head axis.

The second jig 36, shown in FIG. 13, may be used to more confidently align the drill guide with the humeral axis. This jig is secured to the drill guide 25 (which in turn is secured to the drill guide receiver 39 shown in the previous figures) through a clamp 48 (which may merely press-fit or clip onto the pin guide). The jig supports the pin locator 38 on the axis of the drill guide. Each of the frame segments 36a, 36b, 36c and 36d may be slidably secured to the adjacent segments to allow adjustment. For example, frame segment 36b is slidably mounted to frame segment 36c (or 36a) so that the pin locator and frame segment 36b can be translated along a plane in which the humeral head axis lies, to bring the pin locator into contact with the humeral head apex. By fixing the pin locator on the axis of the drill guide, the surgeon can adjust the locator pin to ensure that it contacts the humeral head apex, which in turn ensures that the drill guide is properly aligned with the desired humeral head axis.

FIG. 14 illustrates an additional jig that may be used to facilitate initial placement of the Schanz pins. Under the arthroscopic exploration, the desired initial entry point of the first Schanz pin (13) may be marked, as mentioned above. This additional jig 52 include a pin guide 46 (which may be the same pin guide shown in FIG. 12), a clamp 53 (which may merely press-fit or clip onto the pin guide), a frame 54 which holds the pin locator 55 in coaxial relationship to the pin guide 46. The pin locator 55 is mounted on frame segment 54c is translatable along the common axis of the pin guide and pin locator (sliding frame segment 54b along frame segment 54a through clamp 54d, for example). The surgeon may use this jig to align the first pin with the marked starter hole (created in the arthroscopic inspection), and align the pin locator on the opposite side of the humeral head, at a point on the anatomical neck plane, and lock the jig in place, and then drive the pin through the humeral head. Both placement of the pin guide and the pin locator may be accomplished during the arthroscopic inspection. To facilitate positioning of the pin locator, the surgeon may open the back of the shoulder and pass the pin locator through the gap between the infraspinatus and teres minor muscles. (Jigs 36 and 52 may share interchangeable components. For example, frame segments 54a, b and d may be the same as frame segment 36a, b and d, and jig 36 can be transformed into jig 52 by swapping frame segment 54c for frame segment 36c.)

With the jig 21 and the optional jig 36 in place, as mentioned above, the surgeon inserts the drill bit into the drill guide and rotates the drill bit (preferably operates the drill to rotate the drill bit) to drill a bore hole through the humeral head along the axis of the humeral head. (The surgeon may first use the drill to place a rigid guide wire along the axis of the humeral head, confirm that it properly located, then use the drill to passing a larger cannulated (hollow) drill bit over guide wire to create the desired bore hole.) The hole drilled into the humeral head may be the same size as shafts to be used later in the procedure, or slightly larger to that the hole can accommodate a bushing which will protect the bone surrounding the bore hole from the rotating shaft. After the drill bit has been driven into and through the humeral head, the jig used to position the drill bit may be removed (unless it is to be used to support additional tool placements). The pins 13 and 14 may also be removed. The bore hole provides a central axis portal for passage of various shafts into the shoulder joint. After the bore hole in the humeral head has been drilled, a bushing 60 (see FIGS. 15, 16 and 17) with an outer diameter matching the diameter of the drill bit (and the diameter of the channel) and an inner diameter matching the drill bit or rotating shafts to be held within the bore hole in the humerus, may be inserted in the channel, to protect it during subsequent operations. An additional bushes or sleeves may be inserted within bushing 60 to size the channel for smaller drill bits and rotating shafts.

Figure 15:
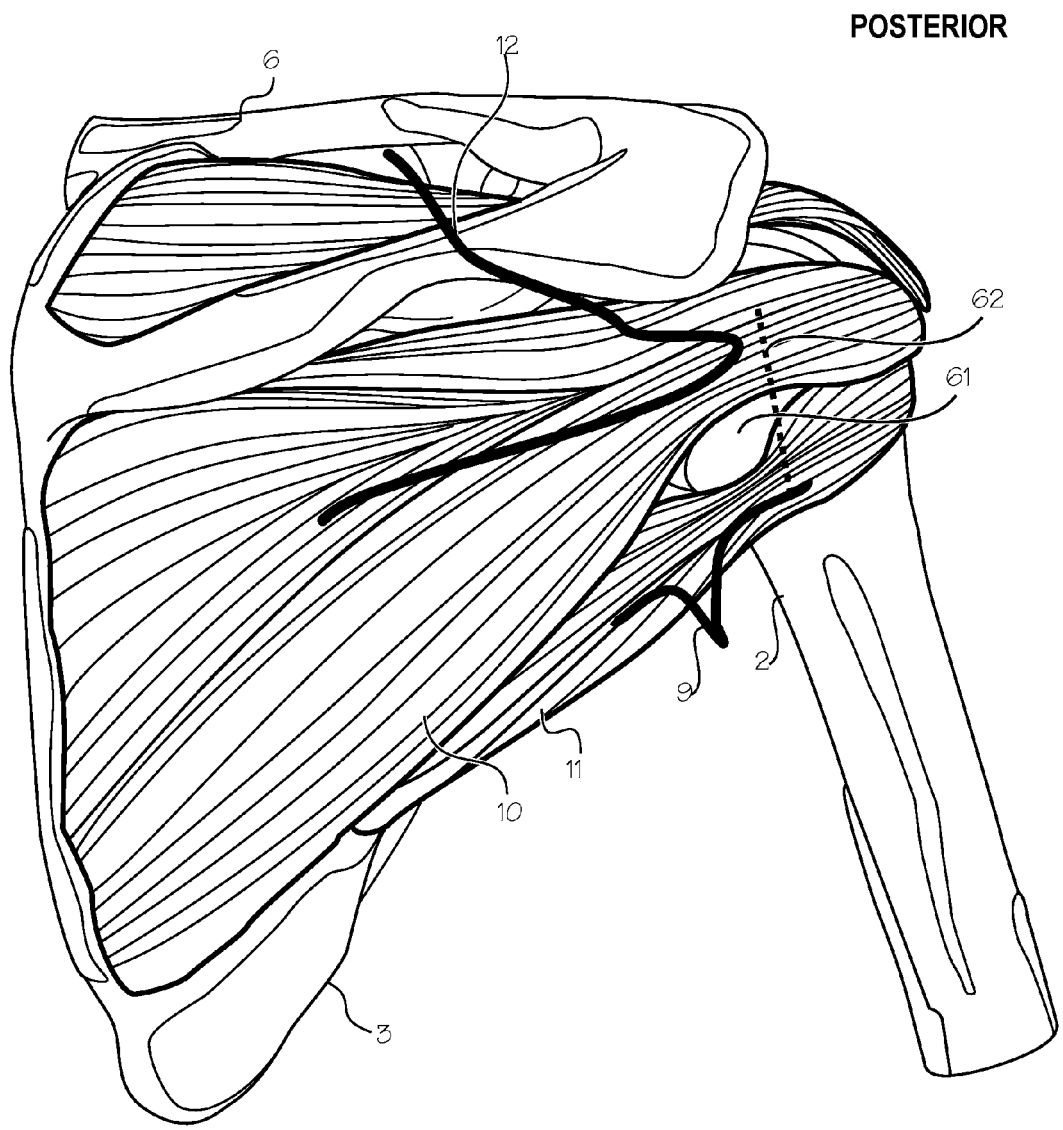
FIG. 15 is a posterior view of the shoulder joint illustrating the method of exposing the glenoid/humerus joint space through the interval between the infraspinatus muscle and teres minor muscle.

FIG. 15 is a posterior view of the shoulder joint illustrating a pathway for insertion of humeral head reamers (for resurfacing) or saws (for replacement), and a humeral head prosthesis into the gleno-humeral joint space. The placement of surgical saws, reamers, other tools, and prostheses such as replacements for the humeral head and glenoid process is accomplished by separating the teres minor and infraspinatus muscles. These procedures may be accomplished without dissecting the infraspinatus muscle (or any other muscle), thus eliminating the possibility of severing the suprascapula nerve 12. They also facilitate joint replacement with smaller incisions and less disruption of other surrounding tissue. Referring again to FIG. 15, the teres minor muscle and infraspinatus muscle are pulled apart to expose the gleno-humeral joint through opening 61. The desired location along the border of the teres minor muscle and infraspinatus muscle is exposed with an incision through the overlying skin at line 62, along an inferior/superior line which is posterior to the gleno-humeral joint space. This opening need only be large enough to pass the blade of the reamer bits, a surgical saw blade, and small parts such as the head of a humeral head prosthesis and the cup of a glenoid fossa prosthesis. To create the gap, the surgeon makes the incision over the proximal to distal axis of the humerus, over the humeral head, and then retracts the skin to maintain the opening, and retracts the teres minor muscle inferiorly and infraspinatus muscle superiorly, and maintains the retractors in place during the surgery. Any necessary long parts or tools (screw drivers, reamer shafts, drill bits and the shaft for the humeral head prosthesis) are passed into the joint through the humeral head channel created as described in relation to FIG. 10, et seq.

Figure 18:
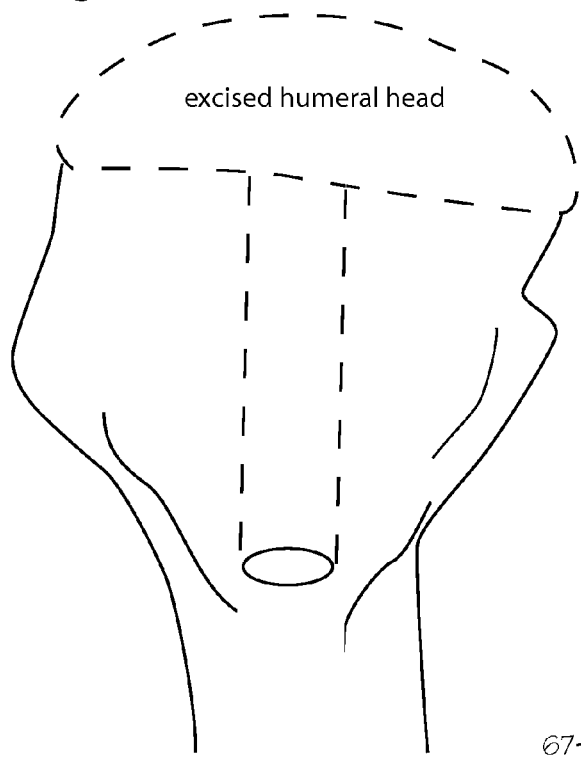
FIGS. 18 and 19 illustrate the flatted humeral head and the prosthesis suitable for implantation through the pathway illustrated in FIG. 15.
Figure 19:
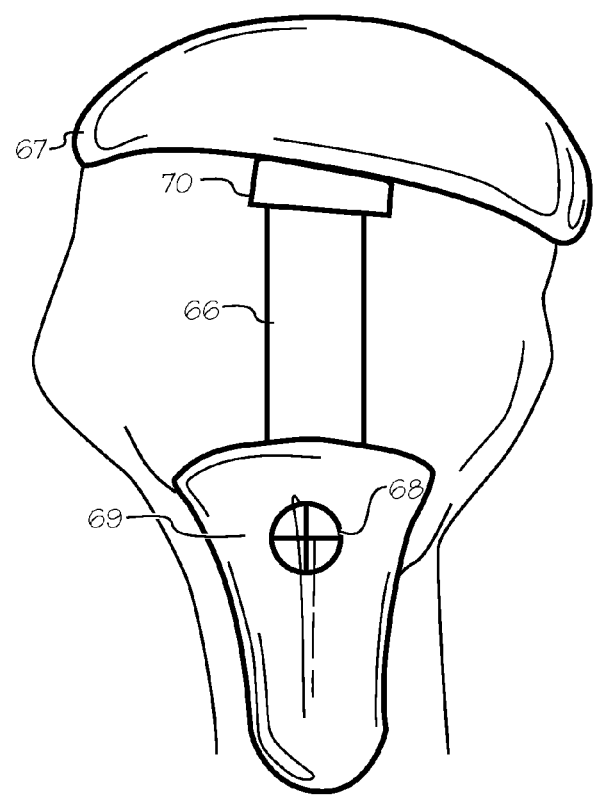

In conventional shoulder replacement surgery, the subscapularis (on the front of the shoulder) muscle must be dissected in order to expose the humeral head and make room for a surgical saw and a metal ball and stem prosthesis. In the following procedure, the ball is inserted through the gap between retracted teres minor and infraspinatus muscles, while the stem is inserted though the channel drilled along the humeral axis as described above. Prior to insertion of the prosthesis, the humeral head may be removed with a surgical saw by passing the narrow blade of a reciprocating surgical saw through the opening 61 between the teres minor muscle and infraspinatus muscle while those muscles are pulled apart with retractors. The saw is operated to cut along the plane established by the Schanz pins (the working plane corresponding to the base of the head of the humerus). If the glenoid fossa is healthy and need not be repaired, the humeral head may be replaced as shown in FIGS. 18 and 19, in which the humeral head (shown in dashed line) is cut along the working plane established by the Schanz pins. The humeral head is removed in typical fashion, with a saw guide and saw.

Figure 17:
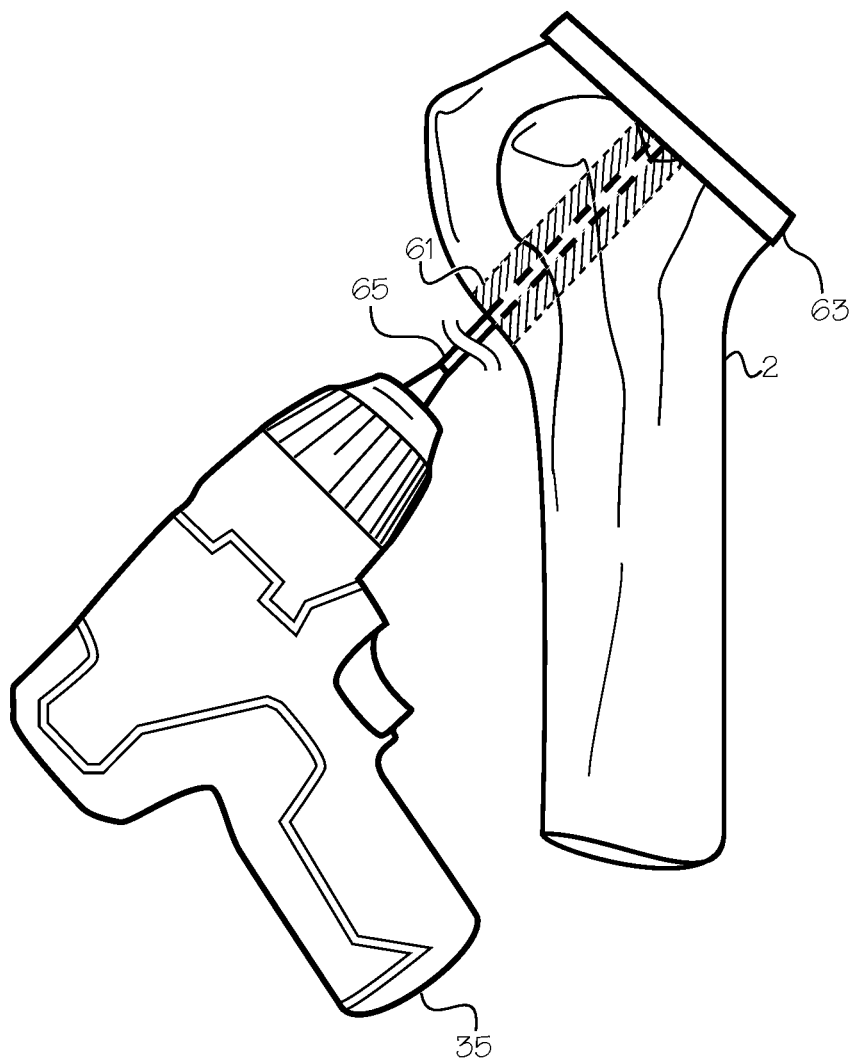

As an alternative to using a saw to remove the humeral head, a reamer can be used, driven from lateral side of the humeral head with a shaft disposed within/passing through the bore hole prepared as described in relation to FIGS. 10 and 11. A shown in FIGS. 16 and 17, a head of a new flat humeral head reamer bit 63 with a flat underside 64 is inserted into the joint space, and then fixed to the shaft 65 disposed within the channel in the humeral head, and rotated by hand or by drill fixed to the shaft. The grinding surface of the flat humeral head reamer bit is disposed on the proximal side (relative to the drill or rotating shaft), while the distal surface is atraumatic and smooth, so that is does not degrade any surfaces of the glenoid fossa, or any tissue surrounding the joint, which it might contact while being rotated to ream the humeral head. The shaft 65 is releasably attachable to the reamer bit 63 (meaning that the shaft can be readily secured to the reamer bit without the use of tools, so that it may be secured to the reamer bit while both the reamer bit and distal end of the shaft are disposed within the shoulder joint.) Using this humeral head reamer, the surgeon reams and grinds the apex of the humeral head away as necessary to fit the prosthetic ball chosen to replace the natural humeral head (the surgeon will typically remove the head down to the anatomical neck plane, as shown in FIG. 17, but may remove more or less to accommodate specific prostheses).

As shown in FIGS. 18 and 19, with the humeral head removed, a prosthesis comprising a stem 66, and ball 67 (corresponding to the excised humeral head), and an anchoring bolt is installed on the humerus. The stem and ball may be joined prior to or after implantation, and the stem and anchoring bolt 68 may be joined prior to or after insertion. In the illustrated method, an opening exposing the gleno-humeral joint is created by retracting the teres minor and infraspinatus muscles, without cutting the muscles. The ball 67 is slipped into place between the retracted muscles, before it is secured to the stem, so that the necessary opening in the gleno-humeral joint and overlying muscles is minimized. The stem 66 is slipped into the channel previously created by the drill, which coincides with the axis of the humeral head, and joined to the ball after it has been placed in the gleno-humeral joint space. After the ball and stem are in place, the anchor bolt 68 is secured to the stem, opposite the head, in the lateral area of the humerus. The anchor bolt is used to tighten the ball against the flat of the humeral head, and may be threaded internally to engage external threads on the stem, through which the overall length of the stem and anchor can be adjusted while tensioning the stem to hold the ball securely on the flat of the femoral head. Alternatively, it can be press fit into the ball 67. A lateral plate 69 may be placed against the lateral surface of the humerus to provide additional support for the anchoring bolt. The receiving bolt 70 shown on the underside of the ball may be threaded, and may be recessed into the undersurface of the ball. Any other attachment means, such as press fit joints, detents, etc. may be used to secure the stem to the ball.

Figure 20:
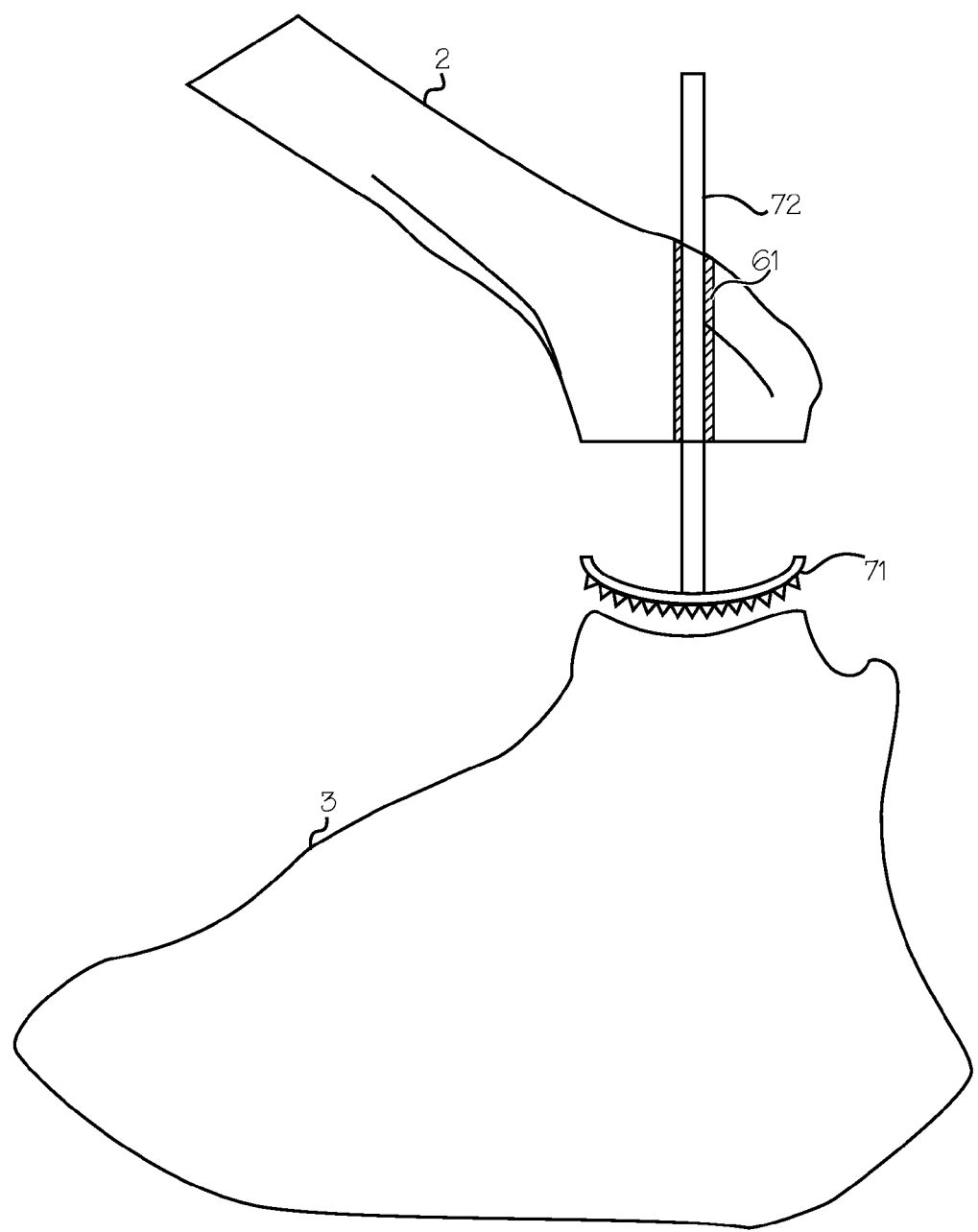
FIG. 20 illustrates placement and use of a glenoid reamer using the pathway illustrated in FIG. 15.
Figure 21:
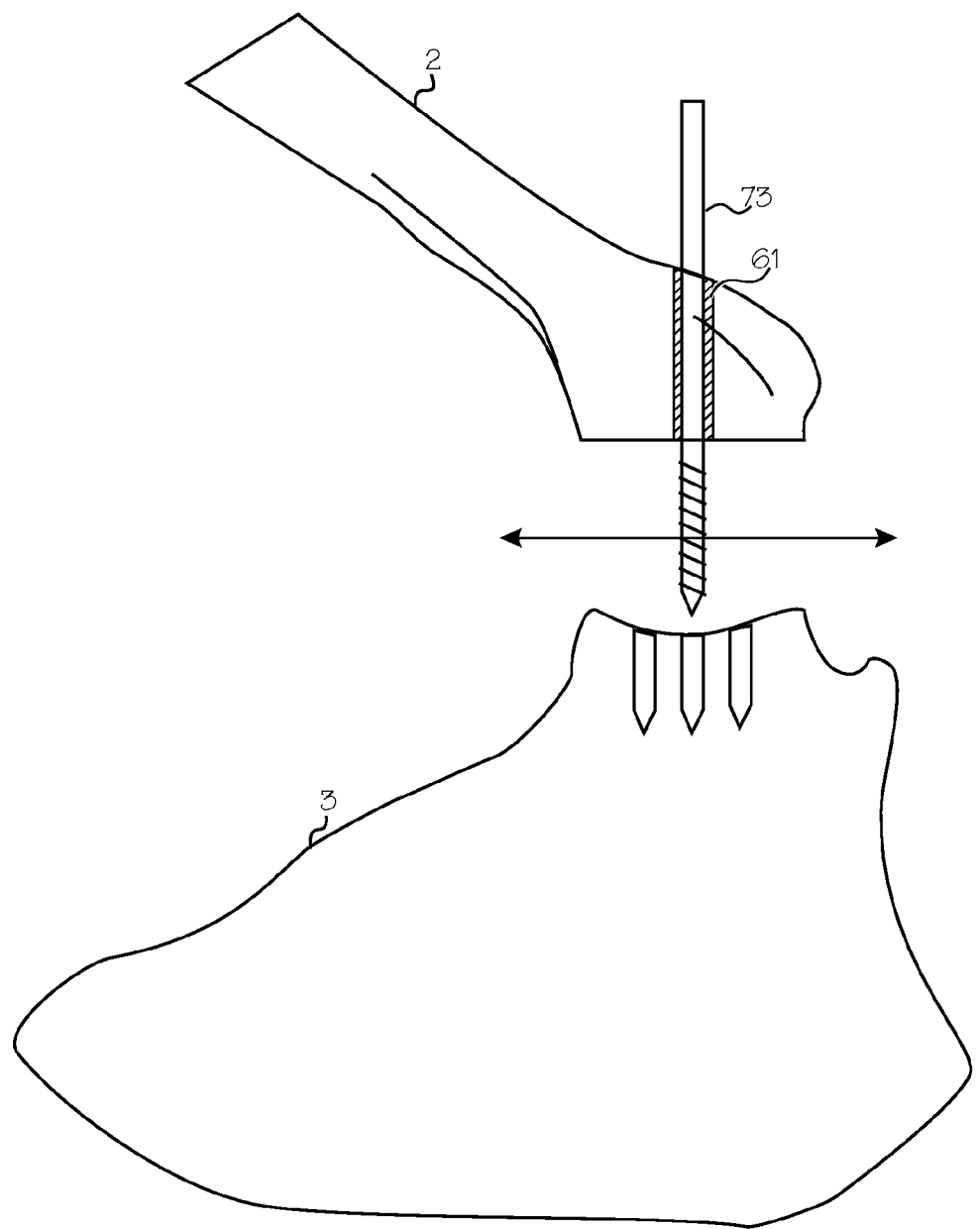
FIG. 21 illustrates the creation of pilot holes in the glenoid fossa with a drill bit disposed in a bore hole along the axis of the humeral head.

Using a similar approach, the glenoid fossa and the humeral head may be resurfaced, and a glenoid prosthesis and a humeral head resurfacing prosthesis may be installed. For example, a head 71 of a glenoid fossa reamer 72 can be inserted into the joint space, and then releasably fixed to a shaft 65 disposed within the channel in the humeral head, and rotated by hand or by a drill fixed to the shaft, and thereafter detached from the shaft and removed from the joint. This is shown in FIG. 20. With the humerus properly positioned (by manipulating and positioning the patient and the shoulder joint), the head of the fossa abrading reamer 72 may be rotated to ream the surface of the glenoid fossa. Reaming may be accomplished as a primary therapy of the glenoid fossa, or to prepare the surface for implantation of a glenoid fossa prosthesis (a cup-shaped replacement socket). If a prosthesis is to be installed, the pilot hole for a central locating pin or keel of the prosthesis can be drilled in the surface of the glenoid fossa. This is shown in FIG. 21, which illustrates the insertion of a drill bit 73 through the channel in the humeral head, along the axis of the humeral head. After the first, center pilot hole is drilled at a location chosen by the surgeon, the additional off-center pilot holes are drilled after placing a template matching the glenoid prosthesis and inserting the drill bit through drill guide holes in the template. The drill bit and drill may be shifted as necessary to align with the template by manipulating the humerus. After the pilot holes are drilled, a glenoid prosthesis may be placed in the prepared glenoid fossa, and screws inserted into the corresponding holes in the prostheses and glenoid process. The screws may be driven using a screw driver inserted through the bore hole in the humeral head. The screws themselves can be passed into the joint through the bore hole in the humeral head. The steps of reaming the glenoid fossa and placing the glenoid prosthesis are performed prior to placement of the humeral head prosthesis.

Figure 22:
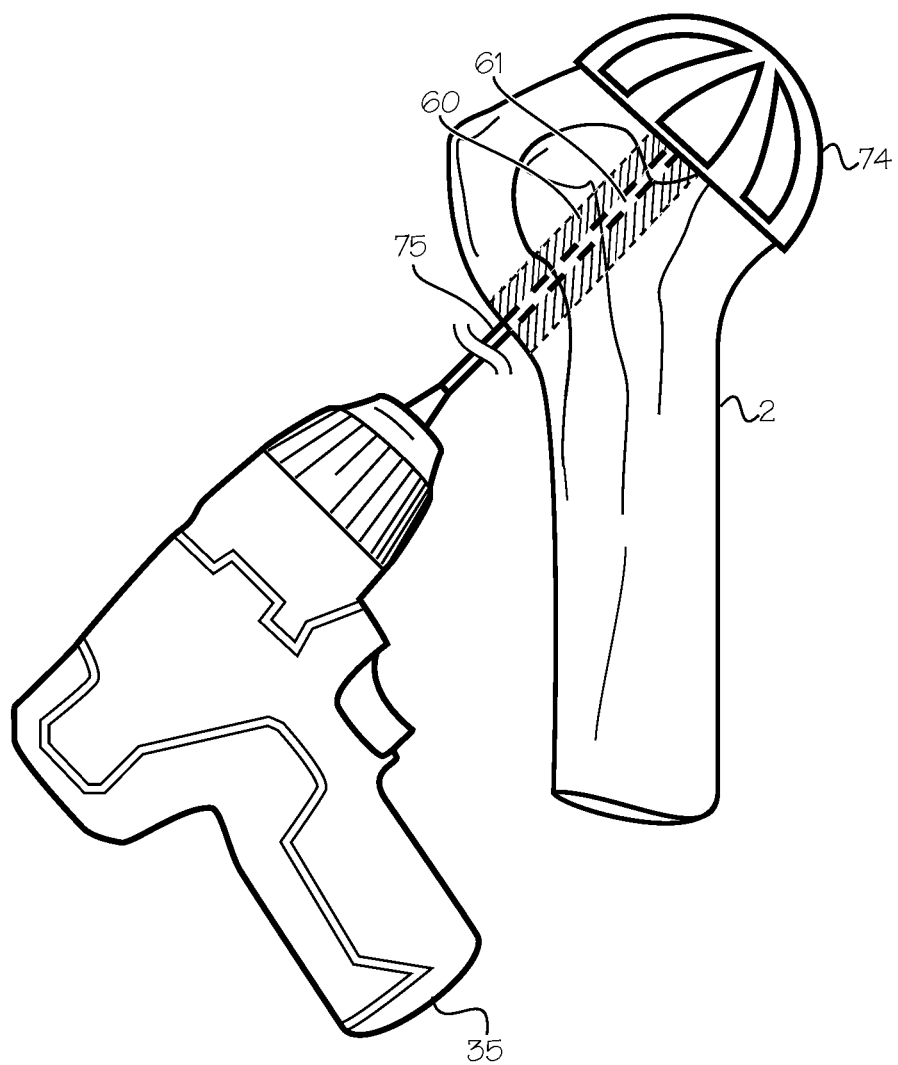
FIG. 22 illustrates the operation of a humeral head reamer with a reamer shaft disposed within a humeral head bore.

For shoulder resurfacing surgery, the humeral head prosthesis is configured to fit over a non-flat, rounded prepared surface of the humeral head (rather that the flat surface described in the earlier figures). This rounded surface may also be prepared using a reamer that is driven by a shaft disposed within the humeral head channel. FIG. 22 illustrates the operation of a humeral head reamer head 74 with a reamer shaft 75 disposed within the humeral head bore, and driven by the drill 35 from the lateral side of the humerus. This reamer head has a concave reaming surface, with a contour matching the concave inner surface of the intended resurfacing prosthesis. With the humeral head reamed to the same shape as the inside of the intended cup-shaped resurfacing prosthesis, the prosthesis may be fitted over the rounded prepared surface and secured as described above with a stem running through the humeral channel and secured with the anchoring member at the lateral surface of the humerus. The prosthesis may also be secured without the stem, by using a typical keel, cement, or a combination of keel and cement.

Shoulder manipulation may augment and facilitate the methods described above. During the arthroscopic portion of the case and when preparing the humeral head, the arm is held in 20 degrees of forward flexion, 40 degrees of abduction and neutral rotation, a fairly normal, slightly forward and outward position. When the glenoid fossa is being prepared, the humerus has to be moved to access the glenoid through the trans-humeral bore hole. That would typically require the humerus to be in 50 degrees of abduction and 30 degrees of external rotation. The shoulder does not have to be dislocated from the joint to remove the humeral head, insert the reamer heads, or insert the prostheses, as it does with conventional shoulder replacement/resurfacing surgery.

The method of performing shoulder resurfacing surgery and replacement surgery, and the devices for facilitating the surgery are described above using exemplary methods and devices. The methods and devices may be generalized, and the benefits of the various inventive steps and methods may be used in isolation, or in combination with each other. Several portions of the method, for example, may be generalized. Part of the method entails performing shoulder surgery by passing a first reamer head into the shoulder joint through a gap formed by retraction between the infraspinatus muscle and the teres minor muscle, operating the reamer to prepare a surface of the shoulder joint for application of a prosthesis to the surface, and passing a first shoulder joint prosthesis into the shoulder joint through the gap between the infraspinatus muscle and the teres minor muscle, and securing the shoulder joint prosthesis to a surface of the shoulder joint. The surgery is thus performed without cutting or releasing muscles and/or tendons from the humerus. Specifically, the surgery is performed without cutting the subscapularis muscle, the infraspinatus muscle, the teres minor muscle, or the tendons attaching these muscles to the humerus.

Another part of the method entails installing a mechanical support for a jig in the humerus, and mounting a jig on the mechanical support. This is done installing one or two pins (Schanz pins, screws, or other support structure) in the humeral head, in the anatomical neck plane, mounting a jig on the pin (or pins) that is shaped to hold a drill guide perpendicular to the anatomical neck plane, an laterally (to the outside) of the shoulder joint, and adjusting the drill guide on the frame to align it with the humeral head axis, and the drilling a bore hole through the humeral head along the humeral head axis, form the lateral aspect of the humeral head to the apex of the humeral head. Through this bore hole, the surgeon can pass a rotatable shaft which can be secured at its distal end to the reamer. The pins may be inserted partially through the humeral head to support the jig, but the rigidity of the jig may be improved by passing the pins entirely through the humeral head and trapping the portion of the pin extending out of the humeral head in pin receiver, where the pin receiver has a bore coaxially aligned with the pin. This alignment is ensured the securing a clamp over the pin (proximally and anteriorly to its entry point in the front of the humerus), where the clamp defines a predetermined axis on which the pin will be held, and where the pin receiver it fixed to the jig such that the bore is coaxially aligned with that axis. Though the method of aligning the humeral head bore hole can be accomplished with one pin so long as the frame can be confidently aligned relative to the pine and the anatomical neck plane, the method is preferably performed using two pins to establish the anatomical neck plane and align the jig relative to the pin and the anatomical neck plane. In this case the first jig and its clamp can be used to position a pin guide in fixed relationship to the first pin to align a second pin for insertion into the humeral head. Where a second pin is used, a second bore in the pin receiver can be used to secure the jig to the distal end of second pin which extends posteriorly from the humeral head, thereby more rigidly securing the jig to the humerus. The surgeon can use yet another jig to initially set the first pin. This additional jig includes a pin guide and a pin locator coaxially aligned with the axis of the pin guide. The surgeon will position the pin guide against the humeral head, at the point selected by the surgeon for entry into the humeral head, and position the pin locator at a corresponding point on the opposite side of the humeral head, to ensure that the pin is driven into or through the humeral head on the anatomical neck plane. Preferably, this part of the method is performed by inserting the pins from the anterior aspect of the humeral head, and driving them through the humeral head until the extend out from the posterior axis of the humeral head. The jigs used to drill the bore hole, and the use of the bore hole to pass the shaft for the reamers, facilitate the method of posterior passage of reamers prosthesis into the joint, but may be in a surgery performed through an anterior approach to limit or eliminate the need to disrupt various tissue around the joint and the need to dislocate the shoulder to remove the humeral head or apply reamers.

The jigs are part of a system for facilitating shoulder replacement or resurfacing surgery, on a shoulder joint characterized by a humerus having a humeral head further characterized by a humeral head axis and a humeral head apex, and a glenoid fossa opposing the humeral head. The system includes the first pin, and preferably a second pin, and one, two or three jigs to assist the surgeon in drilling a bore hole through the humeral head. The system may also include reamer bits, shafts, and prosthesis. In particular, the reamer bits preferable have reaming surfaces which match the contours of the bone-contacting surfaces of the prostheses to be applied.

These steps can be mixed and matched, depending on the condition of the humeral head and glenoid socket. The humeral head can be replaced with or without replacement of the glenoid socket, or with resurfacing or debridement of the glenoid socket, or no treatment of the glenoid socket. When the humeral head is merely resurfaced rather than replaced, the glenoid socket can be replaced, resurfaced, debrided, or untreated. In some cases, the posterior access can be used to pass reamers or debridement tools into the joint in order to debride the humeral head and/or the glenoid fossa without preparing the joint for the installation of prostheses.

Several versions of shoulder surgery have been addressed above. The surgery necessarily entails many options and variations. The exact combination of steps to be used, reamer heads to be used, and prostheses to use will depend on the particular condition of the humeral head and glenoid fossa encountered in each patient. While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other.

I claim:

1. A method for performing shoulder surgery, said method comprising the steps of:
   inserting a first pin in a humeral head of a shoulder joint in an anatomical neck plane of the humeral head;
   mounting a first jig on the first pin, said first jig shaped to hold a drill guide perpendicular to the anatomical neck plane and laterally, relative to the shoulder joint;
   adjusting the drill guide on the first jig to align it with a humeral head axis;
   passing a drill bit through the drill guide and drilling a bore hole through the humeral head, along the humeral head axis, starting from a lateral aspect of the humeral head;
   passing a first reamer head into the shoulder joint through a gap formed by retraction between an infraspinatus muscle and a teres minor muscle;
   passing a rotatable shaft into the bore hole in the humeral head and securing a distal end of the rotatable shaft to the first reamer head;
   operating the first reamer head to prepare a first surface of the shoulder joint for application of a prosthesis to the surface;
   passing a first shoulder joint prosthesis into the shoulder joint through the gap between the infraspinatus muscle and the teres minor muscle, and securing the first shoulder joint prosthesis to the surface of the shoulder joint.

2. The method of claim 1 further comprising the step of:
   securing a second jig to the first jig, said second jig shaped to hold a pin locator in line with an axis of the drill guide when the second jig is secured to the first jig.

3. The method of claim 2 further comprising the step of:
   securing the second jig to the first jig by securing it to the drill guide.

4. The method of claim 2 further comprising the step of:
   adjusting the pin locator to contact an apex of the humeral head prior to drilling the bore hole through the humeral head.

5. The method of claim 2 further comprising the step of:
   marking an apex of the humeral head in an arthroscopic procedure prior to installing the second jig.

6. The method of claim 1 further comprising the steps of:
   providing the first jig with a clamp for grasping the first pin along a predetermined axis of the clamp, and with a pin receiver having a bore coaxially aligned with the predetermined axis of the clamp;
   passing the first pin through the humeral head, securing the clamp over the first pin such that the first pin is held along the predetermined axis of the clamp, and disposing the first pin also within the bore of the receiver.

7. The method of claim 1 further comprising the steps of:
   providing the first jig with a clamp for grasping the first pin and a second pin along first and second predetermined axes of the clamp, and with a pin receiver having first and second pin receiving bores coaxially aligned with the first and second predetermined axes, respectively, of the clamp;
   passing the first pin through the humeral head, securing the clamp over the first pin such that the first pin is held along the first predetermined axis of the clamp, and disposing the first pin also within the first pin receiving bore of the receiver;
   disposing a pin guide in the clamp along the second predetermined axis of the clamp;
   passing the second pin through the pin guide along the second predetermined axis of the clamp, through the humeral head, and into the second pin receiving bore of the pin receiver;
   thereby rigidly securing the first jig to the humeral head.

8. The method of claim 1 further comprising the step of:
   marking a desired location for installation of the first pin on the anatomical neck plane in an arthroscopic procedure prior to installing the first pin.

9. The method of claim 8 further comprising the steps of:
   providing a third jig, said third jig securable to a first pin guide having an axis, said third jig having a pin locator opposing the first pin guide and coaxially aligned with said first pin guide,
   aligning the first pin guide with the desired location for installation of the first pin on an anterior side of the humeral head,
   aligning the pin locator on the anatomical neck plane on a posterior side of the humeral head, and
   using the first pin guide to guide installation of the first pin in the humeral head.

10. The method of claim 9 further comprising the steps of:
    removing the third jig from the first pin guide;
    securing the first jig to the first pin guide;
    securing a second pin guide within a clamp parallel to the first pin guide;
    disposing the second pin guide in the anatomical neck plane and in proximity to the humeral head;
    driving a second pin through the second pin guide and into the humeral head.

11. The method of claim 1 further comprising the step of:
    marking the anatomical neck plane of the humeral head in an arthroscopic procedure prior to installing the first pin.

12. The method of claim 1 further comprising the steps of:
    passing a second reamer head into the shoulder joint through the gap formed by retraction between the infraspinatus muscle and the teres minor muscle;
    securing the distal end of the rotatable shaft to the second reamer head;
    rotating the second reamer head to resurface a glenoid fossa;

passing a second shoulder joint prosthesis into the shoulder joint through the gap between the infraspinatus muscle and the teres minor muscle, and securing the second shoulder joint prosthesis to the humeral head, wherein the step of operating the first reamer head comprises rotating the first reamer head to resurface the humeral head, and wherein the step of securing the first shoulder joint prosthesis comprises securing the first shoulder joint prosthesis to the glenoid fossa.

13. The method of claim 1 further comprising the steps of:

installing a plate on the lateral aspect of the humeral head;

securing a bolt to the first shoulder joint prosthesis and to the plate, thereby securing the first shoulder joint prosthesis in place in the humeral head, and wherein the step of operating the first reamer head comprises rotating the first reamer head to resurface the humeral head.

14. A method for performing shoulder surgery, said method comprising the steps of:

establishing a mechanical support in an anatomical neck plane of a proximal humeral head of the shoulder joint by fixing one or more pins in the humerus, fixing a jig to one or more of the pins, where the jig is shaped to hold a drill guide in perpendicular relationship to the anatomical neck plane;

using the drill guide to drill a bore hole through the humeral head;

inserting a reamer shaft of a reamer into the bore hole;

separating an infraspinatus muscle and a teres minor muscle to expose the shoulder joint;

passing a reamer head of the reamer into the shoulder joint, and attaching the reamer head to the reamer shaft to assemble the reamer;

operating the reamer to prepare a surface of the joint to accept a humero-glenoid prosthesis;

passing a humero-glenoid prosthesis between the separated infraspinatus muscle and the teres minor muscles and into the shoulder joint, securing the humero-glenoid prosthesis to a surface of the shoulder joint.

* * * * *